United States Patent
Egen et al.

(10) Patent No.: US 10,522,768 B2
(45) Date of Patent: Dec. 31, 2019

(54) USE OF TRANSITION METAL CARBENE COMPLEXES IN ORGANIC LIGHT-EMITTING DIODES (OLEDS)

(71) Applicant: UDC Ireland Limited, Dublin (IE)

(72) Inventors: Martina Egen, Dossenheim (DE);
Klaus Kahle, Ludwigshafen (DE);
Markus Bold, Dirmstein (DE);
Thomas Gessner, Heidelberg (DE);
Christian Lennartz, Schifferstadt (DE);
Simon Nord, Roemerberg (DE);
Hans-Werner Schmidt, Bayreuth (DE);
Mukundan Thelakkat, Bayreuth (DE);
Markus Baete, Kulmain (DE);
Christian Neuber, Bayreuth (DE);
Wolfgang Kowalsky, Braunschweig (DE); Christian Schildknecht, Braunschweig (DE); Hans-Hermann Johannes, Braunschweig (DE)

(73) Assignee: UDC Ireland Limited, Dublin (IE)

( * ) Notice: Subject to any disclaimer, the term of this patent is extended or adjusted under 35 U.S.C. 154(b) by 708 days.

(21) Appl. No.: 14/314,753

(22) Filed: Jun. 25, 2014

(65) Prior Publication Data
US 2014/0309428 A1 Oct. 16, 2014

Related U.S. Application Data

(63) Continuation of application No. 11/720,291, filed as application No. PCT/EP2005/012529 on Nov. 23, 2005, now abandoned.

(30) Foreign Application Priority Data

Nov. 25, 2004 (DE) .................. 10 2004 057 072

(51) Int. Cl.
*H01L 51/54* (2006.01)
*C09K 11/06* (2006.01)
*H01L 51/00* (2006.01)
*C07F 15/00* (2006.01)
*H05B 33/14* (2006.01)
*H01L 51/50* (2006.01)

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1044* (2013.01); *C09K 2211/185* (2013.01); *H01L 51/5012* (2013.01); *H01L 51/5016* (2013.01); *H01L 51/5048* (2013.01)

(58) Field of Classification Search
None
See application file for complete search history.

(56) References Cited

U.S. PATENT DOCUMENTS

| | | | |
|---|---|---|---|
| 5,484,922 A | 1/1996 | Moore et al. | |
| 5,503,910 A * | 4/1996 | Matsuura et al. | C09K 11/06 313/504 |
| 6,737,531 B1 | 5/2004 | Dioumaev et al. | |
| 7,393,599 B2 | 7/2008 | Thompson et al. | |
| 7,491,823 B2 | 2/2009 | Thompson et al. | |
| 2004/0121184 A1 | 6/2004 | Thompson et al. | |
| 2005/0031903 A1 | 2/2005 | Park et al. | |
| 2006/0258043 A1 | 11/2006 | Bold et al. | |

FOREIGN PATENT DOCUMENTS

| | | |
|---|---|---|
| WO | 0070655 | 11/2000 |
| WO | 01 41512 | 6/2001 |
| WO | 0215645 | 2/2002 |
| WO | 2005019373 | 3/2005 |
| WO | 2005113704 | 12/2005 |

OTHER PUBLICATIONS

Jazzar, et al., "C—C and C—H Bond Activation Reactions in N-Heterocyclic Carbene Complexes of Ruthenium", Journal of the American Chemical Society, vol. 124, No. 18, XP-002366936, 2002, pp. 4944-4945.
"C—H activation with N-heterocyclic carbene complexes of iridium and rhodium", Journal of the AX chemical society, Dalton Transactions, pp. 3090-3091, XP-002303856, 2002, Danopoulos et al.
"A Theoretical Study of the Activation of C—C and C—H Bonds in Ruthenium N-Heterocyclic Carbene Complexes", XP002366937, Diggle et al., XXIst International Conference on Organometallic Chemistry, Book of Abstracts, Jul. 2004, p. 251.
Thompson, M.E. et al., "Blue and Near-UV Phosphorescence from Iridium Complexes with Cyclometalated Pyrazolyl or N-Heterocyclic Carbene Ligands", 2005, Inorg. Chem., 44:7992-8003.
Francis, Paul S. et al., "Understanding Electrogenerated Chemiluminescence Efficiency in Blue-Shifted Iridium(III)-Complexes: An Experimental and Theoretical Study", 2014, Chem. Eur. J., 20:3322-3332.
Brooks, J. et al., "22.1: Invited Paper: Color Tuning Dopants for Electrophosphorescent Devices: Toward Efficient Blue Phosphorescence from Metal Complexes", 2005, SID 05 Digest, 36:1058.
Hong, M. et al., "Effect of Substituents on the Electronic Structure and Degradation Process in Carbazole Derivatives for Blue OLED Host Materials", Chem. Mater., 2016, 28:5791-5798.
Morello, G.R., "Accurate prediction of emission energies with TD-DFT methods for platinum and iridium OLED materials", J. Mol. Model., 2017, 23:174.

(Continued)

*Primary Examiner* — Marie R. Yamnitzky
(74) *Attorney, Agent, or Firm* — Riverside Law LLP

(57) ABSTRACT

The present invention relates to the use of transition metal-carbene complexes in organic light-emitting diodes (OLEDs), to a light-emitting layer, to a blocking layer for electrons or excitons, or to a blocking layer for holes, each comprising these transition metal-carbene complexes, to OLEDs comprising these transition metal-carbene complexes, to devices which comprise an inventive OLED, and to transition metal-carbene complexes.

14 Claims, No Drawings

(56) References Cited

OTHER PUBLICATIONS

Tavasli M. et al., "Colour tuning from green to red by substituent effects in phosphorescent tris-cyclometalated iridium(III) complexes of carbazole-based ligands: synthetic, photophysical, computational and high efficiency OLED studies", J. Mater. Chem., 2012, 22:6419-6428.

* cited by examiner

USE OF TRANSITION METAL CARBENE COMPLEXES IN ORGANIC LIGHT-EMITTING DIODES (OLEDS)

CROSS-REFERENCE TO RELATED APPLICATIONS

The present application is a continuation of U.S. application Ser. No. 11/720,291, filed May 25, 2007, which is a National Stage (371) of PCT/EP05/12529, filed Nov. 23, 2005, which claims priority to DE 10 2004 057 072.8, filed Nov. 25, 2004.

The present invention relates to the use of transition metal-carbene complexes in organic light-emitting diodes (OLEDs), to a light-emitting layer, to a blocking layer for electrons or excitons, or to a blocking layer for holes, each comprising these transition metal-carbene complexes, to OLEDs comprising these transition metal-carbene complexes, to devices which comprise an inventive OLED, and to transition metal-carbene complexes.

In organic light-emitting diodes (OLEDs), the property of materials to emit light when they are excited by electrical current is utilized. OLEDs are of particular interest as an alternative to cathode ray tubes and liquid-crystal displays for the production of flat visual display units. Owing to the very compact design and the intrinsically low power consumption, devices comprising OLEDs are suitable especially for mobile applications, for example for applications in mobile telephones, laptops, etc.

Numerous materials have been proposed which emit light on excitation by electrical current.

WO 02/15645 relates to OLEDs which have a light-emitting layer which comprises phosphorescent transition metal compounds. The transition metal compounds exhibit electrophosphorescence, especially in the blue region of the visible electromagnetic spectrum. However, the color coordinates of the blue emitted by the complexes disclosed in WO 02/15645 are in need of improvement.

WO 01/41512 relates to OLEDs which have a light-emitting layer which comprises a molecule of the general formula $L_2MX$ where M is more preferably iridium and L is selected from the group consisting of 2-(1-naphthyl)benzoxazole, 2-phenylbenzoxazole, 2-phenylbenzothiazole, 7,8-benzoquinoline, coumarin, thienylpyridine, phenylpyridine, benzothienylpyridine, 3-methoxy-2-phenylpyridine, and tolylpyridine, and X is selected from the group consisting of acetylacetonate, hexafluoroacetylacetonate, salicylidenes, picolinate and 8-hydroxyquinolinate.

WO 00/70655 relates to electroluminescent layers which have, as the light-emitting substance, a phosphorescent organometallic iridium compound or osmium compound. Preference is given to using tris(2-phenylpyridine) iridium as the light-emitting compound.

Even though compounds are already known which exhibit electroluminescence in the blue, red and green region of the electromagnetic spectrum, it is desirable to provide more efficient compounds which are industrially usable. Electroluminescence refers both to electrofluorescence and to electrophosphorescence. In addition, the provision of further compounds for use as materials which block electrons, excitons or holes is of interest.

It is therefore an object of the present application to provide a compound class which is suitable for electroluminescence in the visible region of the electromagnetic spectrum. It is a further object of the present application to provide compounds for use as materials which block electrons, excitons or holes.

These objects are achieved by the use of uncharged transition metal complexes of the general formula I

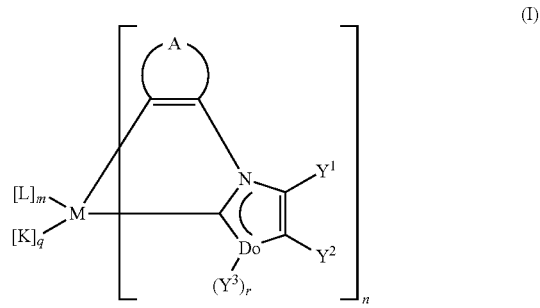

where the variables are each defined as follows:

M is a metal atom selected from the group consisting of Co, Rh, Ir, Nb, Pd, Pt, Fe, Ru, Os, Cr, Mo, W, Mn, Re, Cu, Ag and Au in any oxidation state possible for the particular metal atom;

L is a mono- or dianionic ligand which may be mono- or bidentate;

K is an uncharged mono- or bidentate ligand selected from the group consisting of phosphines; phosphonates and derivatives thereof, arsenates and derivatives thereof; phosphites; CO; pyridines; nitriles, monoolefins and conjugated dienes which form a π-complex with M;

n is the number of carbene ligands, where n is at least 1 and the carbene ligands in the complex of the formula I, when n>1, may be the same or different;

m is the number of ligands L, where m may be 0 or ≥1 and the ligands L, when m>1, may be the same or different;

q is the number of ligands K, where q may be 0 or >1 and the ligands K, when q>1, may be the same or different, where the sum of n+m+q depends upon the oxidation state and coordination number of the metal atom used and upon the denticity and the charge of the ligands, with the condition that n is at least 1;

Do is a donor atom selected from the group consisting of N, O and S;

r is 1 when Do is N and O when Do is O or S;

$Y^1$, $Y^2$ are each independently hydrogen, alkyl, alkenyl, alkynyl, aryl or heteroaryl;

or $Y^1$ and $Y^2$, together with the carbon atoms to which they are bonded, form a six-membered aromatic ring which may comprise one or two nitrogen atoms, and is optionally fused to a further ring which is optionally fused and optionally comprises heteroatoms;

$Y^3$ is hydrogen or alkyl;

or $Y^3$ and $Y^2$, together with the donor atom Do and the carbon atom to which $Y^2$ is bonded, form a five- or six-membered ring which, apart from the donor atom Do, may also comprise a further heteroatom selected from the group consisting of N, O and S;

A is a bridge having three or four atoms, of which one or two atoms may be heteroatoms and the remaining atoms are carbon atoms, so that the group

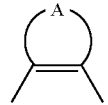

forms a five-membered heteroaromatic ring or six-membered aromatic or heteroaromatic ring, each of which is optionally substituted by substituents selected from the group consisting of alkyl, alkyloxy, alkylthio, aryl, aryloxy, arylthio, halogen, CN, CHO, alkylcarbonyl, arylcarbonyl, carboxyl, alkyloxycarbonyl, aryloxycarbonyl, hydroxysulfonyl, alkyloxysulfonyl, aryloxysulfonyl, $NO_2$ and NO, and optionally fused with a further ring which is optionally fused and optionally comprises heteroatoms, where $Y^1$, together with a group selected from chemical single bond, $C(Y^4)_2$, C(O), O, S, S(O), $SO_2$ and $NY^5$, may optionally form a two-membered bridge B to that carbon atom or heteroatom of the bridge A which is in the α-position to the carbon atom which is bonded to the nitrogen atom of the carbene unit of the carbene ligand;

$Y^4$, $Y^5$ are each independently hydrogen, alkyl, aryl or heteroaryl, and the two $Y^4$ groups in the $C(Y^4)_2$ bridge may be varied independently of one another.

The transition metal complexes of the formula I may be used in any layer of an OLED, and the ligand skeleton or central metal may be varied for adjustment to desired properties of the metal complexes. For example, it is possible to use the transition metal complexes of the formula I in a blocking layer for electrons, a blocking layer for excitons, a blocking layer for holes, a hole-transporting layer, an electron-transporting layer or the light-emitting layer of the OLED. Preference is given to using the compounds of the formula I as emitter molecules in OLEDs.

A bidentate ligand means a ligand which is coordinated at two sites to the transition metal atom M. A monodentate ligand refers to a ligand which coordinates at one site on the ligand to the transition metal atom M.

Depending on the coordination number of the metal M used and on the nature and type of the ligands L and K used, and on the number of carbene ligands, different isomers of the corresponding metal complexes may be present for the same metal M and same type and number of the ligands K and L used and the number of carbene ligands. For example, in the case of complexes having a metal M with the coordination number 6 (i.e. octahedral complexes), for example Ir(III) complexes, both cis/trans isomers when the complexes are of the general composition $MA_2B_4$ and fac-mer isomers (facial/meridional isomers) when the complexes are of the general composition $MA_3B_3$ are possible. In the case of square planar complexes having a metal M with the coordination number 4, for example Pt(II) complexes, cis/trans isomers are possible when the complexes are of the general composition $MA_2B_2$. The variables A and B are each a binding site of a ligand, and not only monodentate, but also bidentate ligands may be present. An unsymmetric bidentate ligand has, according to the above-mentioned general composition, one A group and one B group, a symmetric ligand two A groups or two B groups.

Those skilled in the art understand what is meant by cis/trans and fac-mer isomers. In octahedral complexes, cis isomerism means that the two A groups in complexes of the composition $MA_2B_4$ occupy adjacent corners of an octahedron, while the two A groups in transisomerism occupy mutually opposite corners of an octahedron. In the case of complexes of the composition $MA_3B_3$, three groups of the same type may either occupy the corners of one octahedral face (facial isomer) or a meridian, i.e. two of the three ligand binding sites are trans to one another (meridional isomer). With regard to the definition of cis/trans isomers and fac-mer isomers in octahedral metal complexes, see, for example, J.

Huheey, E. Keiter, R. Keiter, Anorganische Chemie: Prinzipien von Struktur und Reaktivität [Inorganic Chemistry: Principles of Structure and Reactivity], 2nd, newly revised edition, translated into German and extended by Ralf Steudel, Berlin; New York: de Gruyter, 1995, pages 575, 576.

In square planar complexes, cisisomerism means that, in complexes of the composition $MA_2B_2$, both the two A groups and the two B groups occupy adjacent corners of a square, while both A groups and both B groups in the case of trans isomerism each occupy the two diagonally opposite corners of a square. With regard to the definition of cis/trans isomers in square planar metal complexes, see, for example, J. Huheey, E. Keiter, R, Keiter, Anorganische Chemie: Prinzipien von Struktur und Reaktivität, 2nd, newly revised edition, translated into German and extended by Ralf Steudel, Berlin; New York: de Gruyter, 1995, pages 557 to 559.

In addition, the carbene ligand may also be bonded to the metal center in accordance with the formula shown below

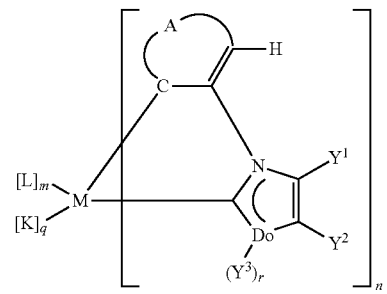

provided that the group

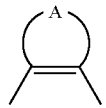

comprises a CH bond which is suitable for cyclometalation and is adjacent to the double bond. In addition, in complexes of the formula I where n>1, one carbene ligand may have the bond to the metal center M shown above and the at least one further carbene ligand may have the bond to the metal center M shown in formula I.

In general, the different isomers of the metal complexes of the formula I may be purified and/or separated by processes known to those skilled in the art, for example by chromatography, sublimation or crystallization.

The present invention therefore relates both to individual isomers of the transition metal-carbene complexes of the formula I and to mixtures of different isomers in any mixing ratio.

Transition metal complexes which comprise carbene ligands are known in the prior art. For instance, Gründemann et al., J. Am. Chem. Soc., 2002, 124, 10473 to 10481 and Danapoulos et al., J. Chem. Soc., Dalton Trans., 2002, 3090 to 3091 relate to iridium complexes which comprise a carbene ligand having the following structural unit

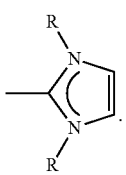

Hitchcock et al. J. Organomet. Chem., 1982, 239, C 26-C 30 disclose iridium(III) complexes which have three monoanionic carbene ligands and the following structural formula

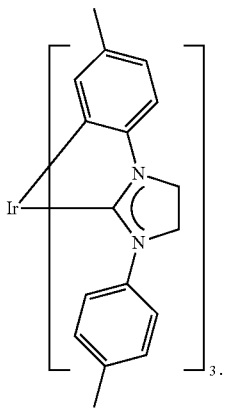

However, none of the documents mentioned disclose luminescence properties, especially electroluminescence properties, of the compounds disclosed or their use in OLEDs.

Yam et al., Chem. Commun. 1989, 2261 to 2262 and Yam et al., J. Chem. Soc. Dalton Trans., 2001, 1911 to 1919 disclose ruthenium complexes which have a carbene ligand. The photophysical properties of these carbene ligands, including the photoluminescence of the complexes, was investigated in the documents specified. However, no remarks are made relating to use of these complexes nor do the documents comprise remarks relating to the electroluminescence of the compounds investigated.

Che et al., Organometallics 1998, 17, 1622 to 1630 relates to cationic Re complexes which have a carbene ligand having the following structural unit

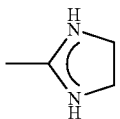

These complexes exhibit photoluminescence. However, use of the Re complexes and the investigation of the electroluminescence behavior of the complexes is not disclosed.

U.S. Pat. Nos. 6,160,267 and 6,338,977 relate to a molecular light-emitting diode which changes its color depending on vapors surrounding it. This electrode has a sensor-emitter layer which comprises a neutral platinum complex, in which platinum is coordinated by two negatively charged ligands selected from the group consisting of $CN^-$, $NO_2^-$, $NCO^-$, $NCS^-$, $Cl^-$, $Br^-$, $I^-$ and oxalate, and the two further ligands are selected from at least one and at most two arylisonitrile groups and a Fischer carbene complex which has the formula $=C(Y)-NH-C_6H_4$-alkyl, where Y is O-alkyl, NH-alkyl or N(alkyl)$_2$. The essential feature of the Pt complexes disclosed in U.S. Pat. Nos. 6,160,267 and 6,338,977 is the presence of at least one arylisonitrile group.

The suitability of transition metal-carbene complexes of the formula I according to the present invention in OLEDs, especially as light-emitting substances in OLEDs, the substances of this structure type of the formula I being suitable for electroluminescence in the visible region of the electromagnetic spectrum, is mentioned in none of the aforementioned documents.

It has thus been found that the transition metal complexes of the formula I according to the present application in OLEDs, especially as light-emitting substances in OLEDs, are suitable for the production of displays.

The transition metal-carbene complexes of the general formula I used in accordance with the invention preferably have a metal atom M selected from the group consisting of Rh, Ir, Pd, Pt, Ru and Os, preference being given to Rh(III), Ir(III), Pd(II), Pt(II), Ru(II), Ru(IV) and Os(IV). Metal atoms used with particular preference are Rh, Ir, Pt and Ru, preferably as Rh(III), Ir(III), Pt(II), Ru(III) and Ru(IV). Very particular preference is given to using Ir or Pt as the metal atom M, preferably as Ir(III) or Pt(III), most preferably Ir(III).

Suitable mono- or dianionic ligands L, preferably monoanionic ligands L, which may be mono- or bidentate are any ligands used customarily as mono- or bidentate, mono- or dianionic ligands.

Suitable monoanionic monodentate ligands are, for example, halides, in particular $Cl^-$ and $Br^-$, pseudohalides, in particular $CN^-$, cyclopentadienyl ($Cp^-$), alkyl radicals which are bonded via a sigma bond to the transition metal M, for example $CH_3$, alkylaryl radicals which are bonded via a sigma bond to the transition metal M, for example benzyl.

Suitable monoanionic bidentate ligands are, for example, acetylacetonate and derivatives thereof, picolinate, Schiff bases, amino acids and tetrakis(1-pyrazolyl)borates, and the bidentate monoanionic ligands specified in WO 02/15645, of which preference is given to acetylacetonate and picolinate.

Suitable uncharged mono- or bidentate ligands have already been specified above. Preferred uncharged monodentate ligands are selected from the group consisting of $PPh_3$, $P(OPh)_3$, $AsPh_3$, CO, optionally substituted pyridines, nitriles and derivatives thereof. Suitable uncharged mono- or bidentate ligands are preferably 1,4-diphenyl-1,3-butadiene, 1-phenyl-1,3-pentadiene, 2,4-hexadiene, cyclooctene, $\eta^4$-cyclooctadiene and $\eta^2$-cyclooctadiene (in each case 1,3 and 1,5) and also optionally substituted phenanthrolines.

In the transition metal-carbene complexes of the formula I used in accordance with the invention, preference is given to n being at least 2, in which case the carbene ligands may be the same or different, and to m and q each being 0 or >1, and the ligands L and K when m>1 or q>1 may each be the same or different. The variables M, L, K, Do, r, $Y^1$ to $Y^5$ and A are each as already defined above.

In the transition metal-carbene complexes of the formula I used in accordance with the invention, preference is also given to n being at least 2, in which case the carbene ligands may be the same or different, and to m and q each being 0. The variables M, L, K, Do, r, $Y^1$ to $Y^5$ and A here too are each as already defined above.

In addition, preference is given in the transition metal-carbene complexes of the formula I used in accordance with the invention to n being at least 2, and to the carbene ligands being the same and to m and q each being 0. The variables M, L, K, Do, r, $Y^1$ to $Y^5$ and A are again each as already defined above.

The number n of carbene ligands in uncharged transition metal complexes, in which, for example, the transition metal atoms Ir(III), Rh(III) or Ru(III) have a coordination number of 6, is from 1 to 3, preferably 2 or 3, more preferably 3. When n is >1, the carbene ligands may be the same or different, preferably the same.

When no uncharged ligands K are present, taking into account the coordination number of the Ir(III), Rh(III) or Ru(III), the number m of monoanionic ligands L in the aforementioned case is accordingly 4, 2 or 0, preferably 2 or 0, more preferably 0. When m is >1, the ligands L may be the same or different, preferably the same.

The number n of carbene ligands in transition metal complexes in which, for example, the transition metal atoms Pt(II) or Pd(II) have a coordination number of 4 is 1 or 2, preferably 2. When n is >1, the carbene ligands may be the same or different, preferably the same.

When no uncharged ligands K are present, taking into account the coordination number of the Pt(II) or Pd(II), the number m of monoanionic ligands L in the aforementioned case is accordingly 2 or 0, more preferably 0. When m is >1, the ligands L may be the same or different, preferably the same.

The number q of uncharged ligands K is dependent upon whether the coordination number 6, for example for Ir(III), Rh(III) or Ru(III), or 4, for example for Pt(II) or Pd(II), has already been attained with the aid of the carbene ligands and the ligands L. When, in the case that Ir(III), Rh(III) or Ru(III) are used, n equals three, q assumes a value of 0. When, in the case that Pt(II) or Pd(II) are used, n equals 2, q likewise assumes a value of 0.

In the context of the present application, the terms aryl, heteroaryl, alkyl, alkenyl and alkynyl are each defined as follows:

Aryl is a radical having a basic skeleton of from 6 to 30 carbon atoms, preferably from 6 to 18 carbon atoms, which is formed from an aromatic ring or a plurality of fused aromatic rings. Suitable basic skeletons are, for example, phenyl, naphthyl, anthracenyl or phenanthrenyl. This basic skeleton may be unsubstituted (i.e. that all carbon atoms which are substitutable bear hydrogen atoms), or be substituted at one of, a plurality of, or all, substitutable positions of the basic skeleton. Suitable substituents are, for example, alkyl radicals, preferably alkyl radicals having from 1 to 8 carbon atoms, more preferably methyl, ethyl or isopropyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear one double bond, more preferably alkenyl radicals having one double bond and from 1 to 8 carbon atoms, or groups having donor or acceptor action. Groups having donor action include groups which have a +I and/or +M effect, and groups having acceptor action include groups which have a -I and/or -M effect. Suitable groups having donor or acceptor action are halogen radicals, preferably F, Cl, Br, more preferably F, alkoxy radicals, aryloxy radicals, carbonyl radicals, ester radicals, amine radicals, for example alkyl-, dialkyl-, aryl-, diarylamine radicals or else diarylamine radicals having bridged aryl radicals such as 1-carbazolyl, amide radicals, $CH_2F$ groups, $CHF_2$ groups, $CF_3$ groups, CN groups, thio groups or SCN groups. When the aryl radicals are substituted, they most preferably bear substituents selected from the group consisting of methyl, F, Cl, aryloxy and alkoxy. Aryl is preferably a $C_6$-$C_{18}$-aryl radical, more preferably a $C_6$-aryl radical, which is optionally substituted by at least one of the aforementioned substituents. More preferably, the $C_6$-$C_{18}$-aryl radical, preferably $C_6$-aryl radical, has no, one or two of the aforementioned substituents, and, in the case of one substituent, it is arranged in the ortho-, meta- or para-position to the further bonding site of the aryl radical; in the case of two substituents, they may each be arranged in the meta-position or ortho-position to the further bonding site of the aryl radical, or one radical is arranged in the ortho-position and one radical in the meta-position, or one radical is arranged in the ortho- or meta-position and the further radical is arranged in the para-position.

Heteroaryl refers to radicals which differ from the above-specified aryl in that at least one carbon atom in the basic aryl skeleton has been replaced by a heteroatom. Preferred heteroatoms are N, O and S. Most preferably, one or two carbon atoms of the basic aryl skeleton have been replaced by heteroatoms. Especially preferably, the basic skeleton is selected from systems such as pyridine and five-membered heteroaromatics such as pyrrole or furan. The basic skeleton may be substituted at one of, a plurality of, or all, substitutable positions of the basic skeleton. Suitable substituents are the same as have already been specified under the definition of aryl.

Alkyl refers to a radical having from 1 to 20 carbon atoms, preferably from 1 to 10 carbon atoms, more preferably from 1 to 8 carbon atoms. The alkyl may be branched or unbranched and optionally be interrupted by one or more heteroatoms, preferably Si, N, O or S, more preferably N, O or S. In addition, the alkyl may be substituted by one or more of the substituents specified under the definition of aryl. It is likewise possible that the alkyl bears one or more aryl groups. In this context, all of the above-listed aryl groups are suitable. More preferably, alkyl is selected from the group consisting of methyl, ethyl, n-propyl, isopropyl and tert-butyl.

Alkenyl refers to a radical which corresponds to the aforementioned alkyl having at least two carbon atoms, with the difference that at least one C—C single bond of the alkyl, where possible, has been replaced by a C—C double bond. The alkenyl preferably has one or two double bonds.

Alkynyl accordingly refers to a radical which corresponds to the aforementioned alkyl having at least two carbon atoms, with the difference that at least one C—C single bond of the alkyl, where possible, has been replaced by a C—C triple bond. The alkynyl preferably has one or two triple bonds.

The variables $Y^1$ and $Y^2$ are each independently hydrogen, alkyl, aryl, heteroaryl or alkenyl.

$Y^1$ is preferably hydrogen. $Y^2$ is preferably hydrogen or alkyl, more preferably hydrogen, methyl, ethyl, n-propyl, isopropyl or tert-butyl.

In a further preference, $Y^1$ and $Y^2$, together with the carbon atoms to which they are bonded, form a six-membered aromatic ring which may comprise one or two nitrogen atoms. This may be fused to a further, optionally fused and optionally heteroatom-comprising ring. In this case, the heteroatoms may be part of the ring or be bonded to the ring (in the "exo-position").

Examples of corresponding fused substructures of the carbene ligands are shown below:

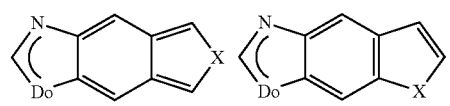

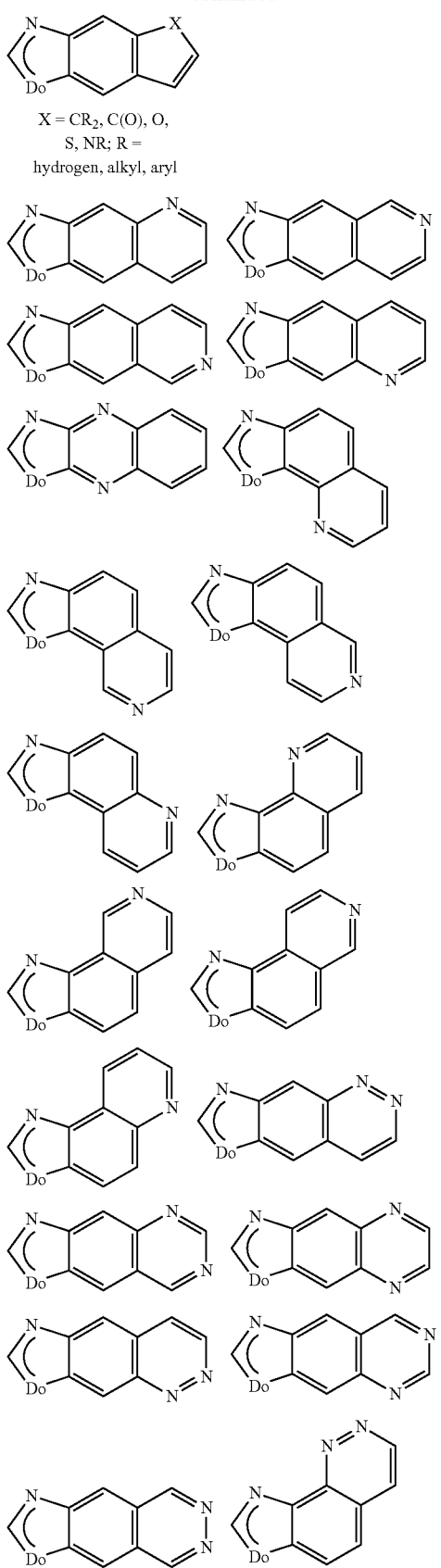
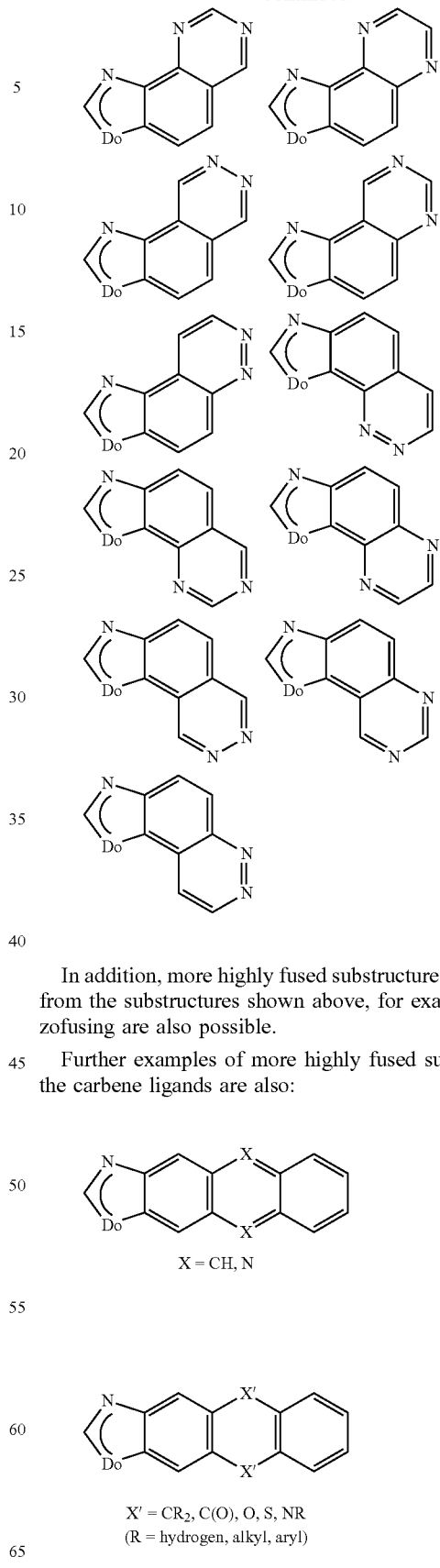
In addition, more highly fused substructures which derive from the substructures shown above, for example, by benzofusing are also possible.
Further examples of more highly fused substructures of the carbene ligands are also:
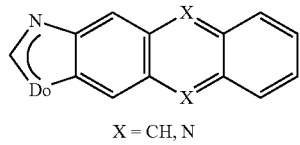
X = CH, N
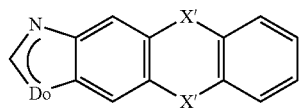
X' = CR₂, C(O), O, S, NR
(R = hydrogen, alkyl, aryl)

Preferred substructures of the carbene ligands are:

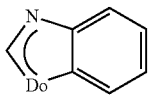 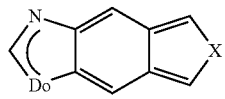

X = O, S

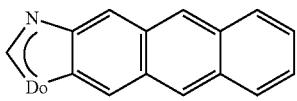

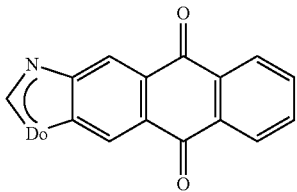

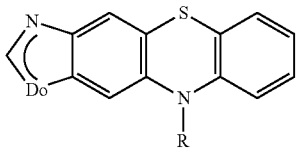

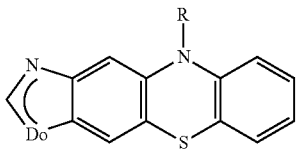

R = hydrogen, alkyl, aryl

In addition, $Y^3$ and $Y^2$, together with the donor atom Do and the carbon atom to which $Y^2$ is bonded, may form a five- or six-membered ring which, apart from the donor atom Do, may also comprise one further heteroatom selected from the group consisting of N, O and S. In this ring, $Y^2$ (together with $Y^1$) may already be part of an optionally (more highly) fused aromatic ring, for instance in the above-listed substructures of the carbene ligands, or $Y^2$ is a (formally) independent radical which, with $Y^3$, forms a further substructure of the carbene ligands.

Since, in the aforementioned case, the (formal) presence of the $Y^3$ radical is obligatory, the only possible donor atom is a nitrogen atom. Examples of corresponding substructures in the carbene ligands are:

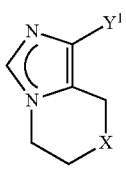 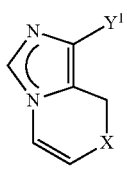 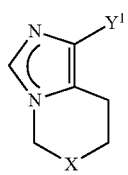

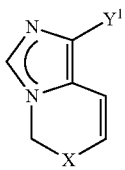 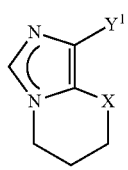 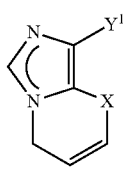

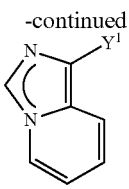

X = CR$_2$, O, S, NR (R = hydrogen, alkyl, aryl)

Preferred substructures are:

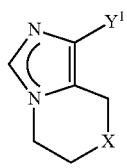 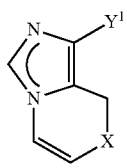 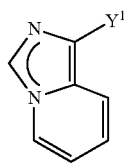

where X is a CH$_2$ group or an oxygen atom.

When $Y^1$ and $Y^2$ additionally, as detailed above, form an optionally more highly fused aromatic ring, this results, for example, in the substructures of the carbene ligands shown below:

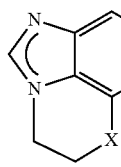 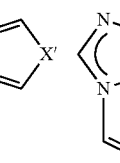

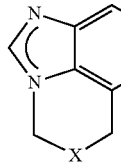 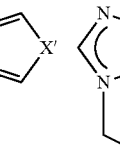

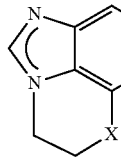 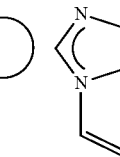

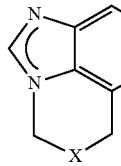 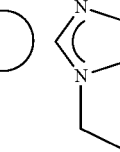

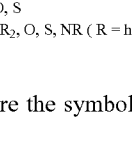 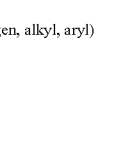

X' = O, S
X = CR$_2$, O, S, NR ( R = hydrogen, alkyl, aryl)

where the symbol

represents a possible fusion of the benzene ring as detailed above. This symbol is preferably defined as one of the fragments

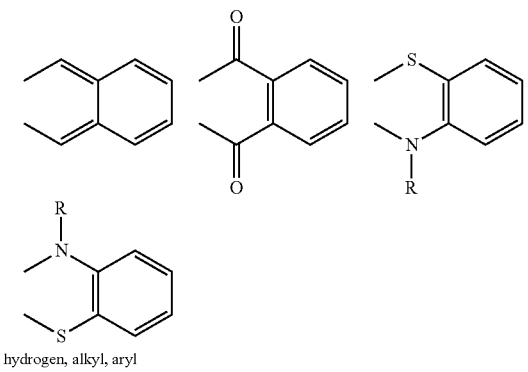

Preferred substructures are:

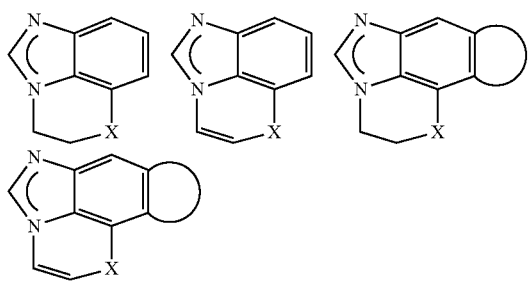

where the symbol

is preferably as defined above and X is a CH$_2$ group or an oxygen atom.

The variable A in formula I is a bridge having three or four atoms, of which one or two atoms may be heteroatoms and the remaining atoms are carbon atoms, so that the group (also referred to hereinbelow as "G")

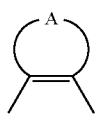

forms a five- or six-membered heteroaromatic ring or a benzene ring. Possible heteroatoms are in particular O, N and S.

Suitable five-membered heteroaromatic rings in the definition of the group G are listed below:

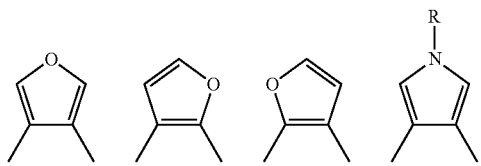

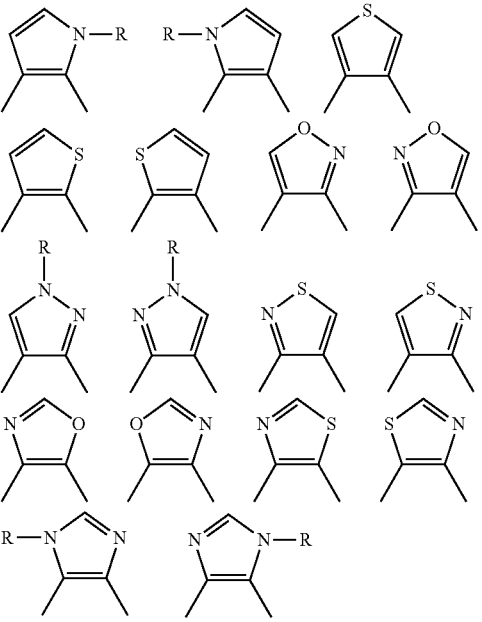

where R is hydrogen, alkyl, alkenyl, alkynyl, aryl or heteroaryl, as defined above, and the ring nitrogen atom, when R is heteroaryl, is bonded via a carbon atom or optionally via a heteroatom, suitable for this purpose, of the heteroaryl.

Suitable six-membered heteroaromatic rings in the definition of the group G are:

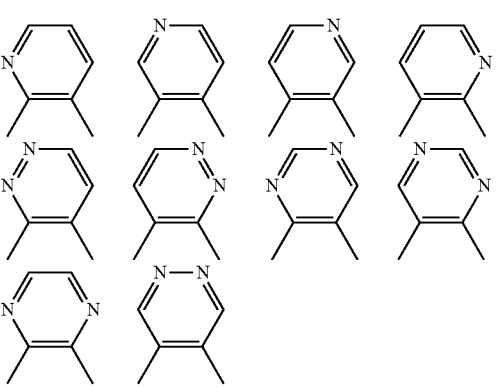

For the group G, preference is given to:

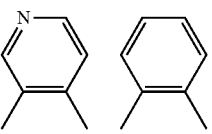

The group G may be substituted by substituents selected from the group consisting of alkyl, alkyloxy, alkylthio, aryl, aryloxy, arylthio, halogen, CN, CHO, alkylcarbonyl, arylcarbonyl, carboxyl, alkyloxycarbonyl, aryloxycarbonyl, hydroxysulfonyl, alkyloxysulfonyl, aryloxysulfonyl, NO$_2$ and NO. When the substituents mentioned comprise heteroatoms, they are bonded to the group G typically via carbon atoms of the group G. However, the bonding may also take place via suitable heteroatoms of the group G.

Preferred substituted groups G are:

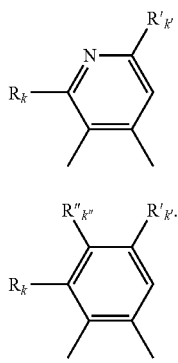

(Ga)

(Gb)

Examples of such more highly fused groups G are:

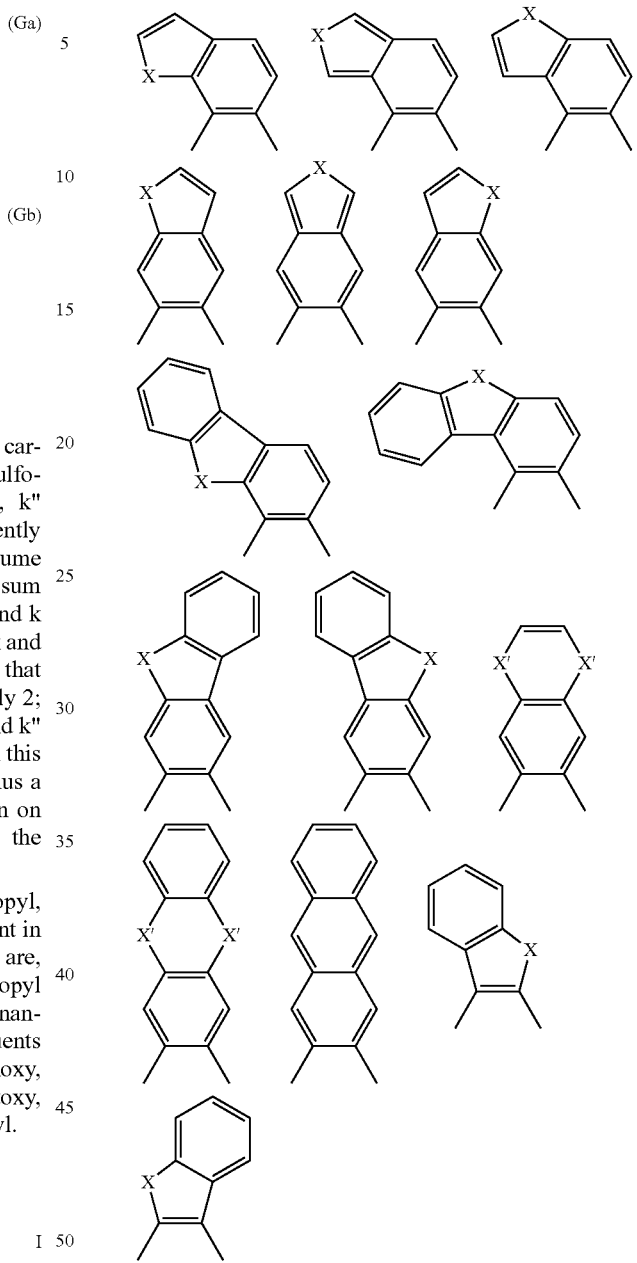

where R″ is CN, CHO, alkylcarbonyl, arylcarbonyl, carboxyl, alkyloxycarbonyl, aryloxycarbonyl, hydroxysulfonyl, alkyloxysulfonyl, aryloxysulfonyl, NO$_2$ or NO, k″ assumes values of 0 or 1, R and R' are each independently alkyl or halogen, in particular fluorine, and k and k' assume values of 0 or 1, with the proviso that, in group (Ga), the sum of k and k' is 1 or 2 and, in group (Gb), the sum of k and k is 1 or 2 when k″ assumes a value of 0, and the sum of k and k″ is 0, 1 or 2 when k″ assumes a value of 1. In the case that k″ assumes a value of 0, the sum of k and k' is preferably 2; in the case that k″ assumes a value of 1, the sum of k and k″ is preferably 0 or 2. A value of 0 for k, k' or k″ means in this context that none of the R, R' or R″ substituents and thus a hydrogen atom is present at the corresponding position on the ring. When k and k'each assume a value of 1, the substituents are preferably the same.

For R and R', alkyl is in particular methyl, ethyl, n-propyl, isopropyl and tert-butyl. Alkyl and aryl which are present in the corresponding radicals of the definition of R″ are, respectively, in particular methyl, ethyl, n-propyl, isopropyl and tert-butyl, and phenyl, naphthyl, anthracenyl or phenanthrenyl, each of which may be substituted by substituents selected from the group consisting of methyl, F, Cl, phenoxy, methoxy, ethoxy, n-propoxy, isopropoxy and tert-butoxy, and preference is given to optionally substituted phenyl.

In particular, such substituted groups include:

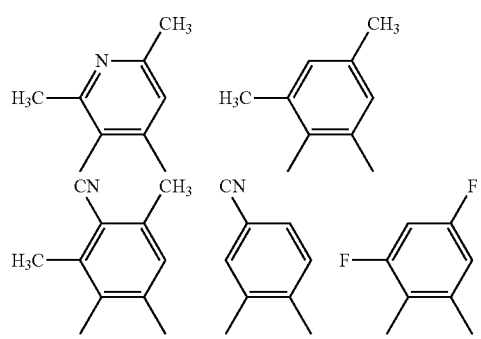

I where X is O, S or NR where R is hydrogen, alkyl or aryl, and the two X' are each independently a carbonyl group, CR$_2$ group, O, S or NR where R is hydrogen, alkyl or aryl.

Preferred fused groups G are:

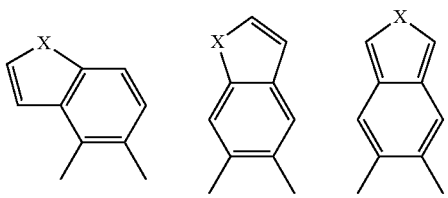

n addition, the group G may also be fused to a further, optionally heteroatom-comprising ring, in which case the latter ring may itself be fused again.

-continued

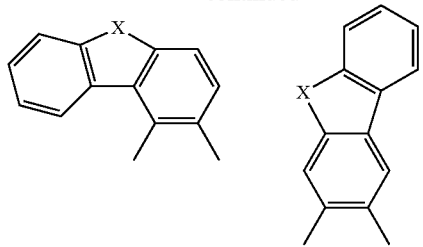

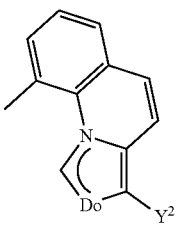

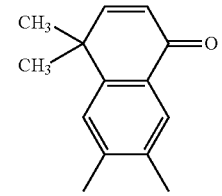

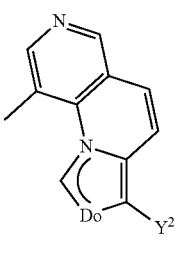

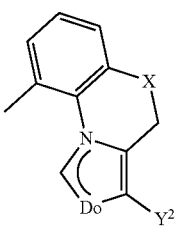

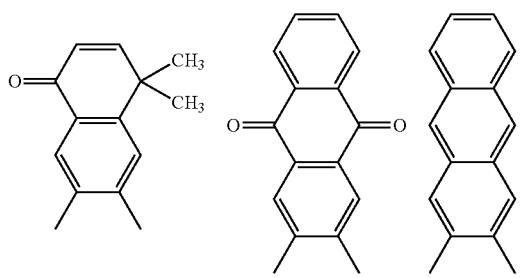

where X is defined as O, S or NR where R is hydrogen, alkyl or aryl, preferably hydrogen or alkyl.

In addition, $Y^1$, together with a group selected from chemical single bond, $C(Y^4)_2$, C(O), O, S, S(O), $SO_2$ and $NY^5$, may form a two-membered bridge B to that carbon atom or heteroatom of the bridge A which is in the α-position to the carbon atom which is bonded to the nitrogen atom of the carbene unit of the carbene ligand. $Y^4$ and $Y^5$ are each independently alkyl, aryl or heteroaryl each as defined above, or hydrogen. The two $Y^4$ in the bridge $C(Y^4)_2$ may be varied independently of one another, but they are preferably the same. More preferably, the two $R^4$ radicals are two hydrogen atoms or two methyl groups.

Formally, such substructures can be represented as:

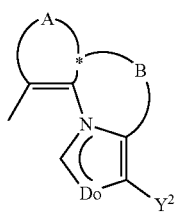

where the asterisk denotes the carbon atom or suitable heteroatom, in the α-position to the N-bonded vinylic carbon atom, of the bridge A, and B denotes the bridge composed of $Y^1$ and chemical single bond, $C(Y^4)_2$, C(O), O, S, S(O), $SO_2$ or $NY^5$. Examples of such substructures are:

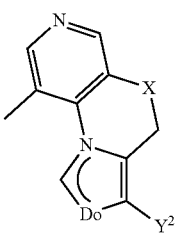

In the formulae (Ba) and (Bb), the bridge B in each case consists of an ethylenediyl unit, in the formulae (Bc) and (Bd) in each case of a-$CH_2$—X— unit in which X is defined as $C(Y^4)_2$, C(O), O, S, S(O), $SO_2$ or $NY^5$.

When $Y^1$ and $Y^2$ additionally form an optionally fused aromatic ring, for example a benzene ring, this results, for instance, in the substructures shown below:

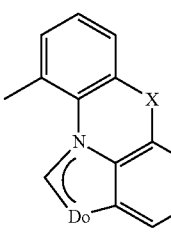

-continued (Bf)

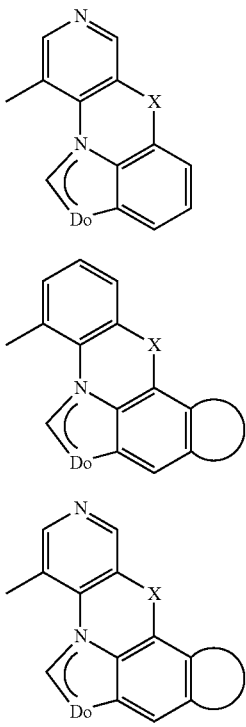

(Bg)

(Bh)

where the bridge B is in some cases part of the benzene ring. X is in turn a chemical single bond, $C(Y^4)_2$, C(O), O, S, S(O), $SO_2$ or $NY^5$, and the symbol

as before is a fusion of the benzene ring.

Preference is given here too to this symbol having the definition of the fragments

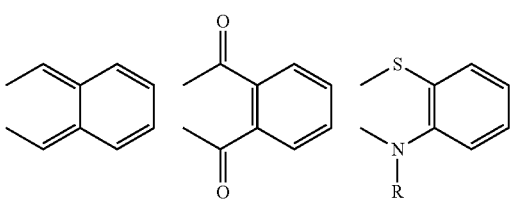

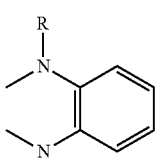

R = hydrogen, alkyl, aryl

Preferred substructures are:

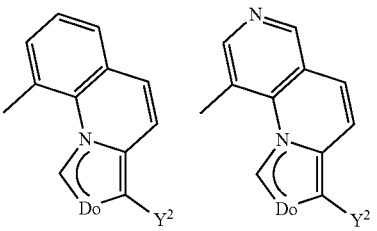

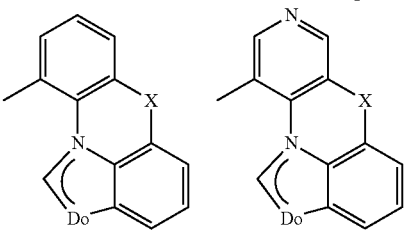

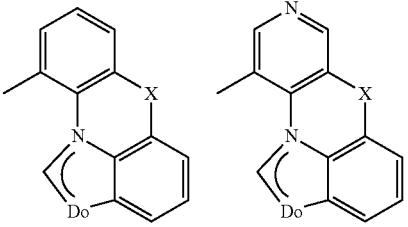

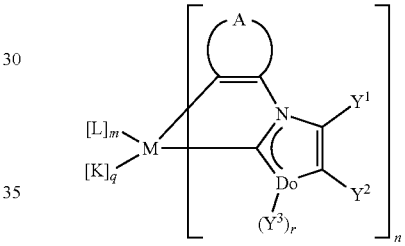

where X is in particular O, S, a $C(CH_3)_2$ or $SO_2$ group.

In the context of the present invention, uncharged transition metal-carbene complexes of the general formula I $$\left[ [L]_m \underset{[K]_q}{\overset{}{\diagup}} M \diagdown \begin{matrix} A \\ \diagdown \\ N \\ \diagup \\ Do \end{matrix} \begin{matrix} Y^1 \\ \\ Y^2 \end{matrix} \right]_n \quad (I)$$

$(Y^3)_r$ are also claimed, where the variables are each defined as follows:

M is a metal atom selected from the group consisting of Co, Rh, Ir, Nb, Pd, Pt, Fe, Ru, Os, Cr, Mo, W, Mn, Re, Cu, Ag and Au in any oxidation state possible for the particular metal atom;

L is a mono- or dianionic ligand which may be mono- or bidentate;

K is an uncharged mono- or bidentate ligand selected from the group consisting of phosphines; phosphonates and derivatives thereof, arsenates and derivatives thereof; phosphites; CO; pyridines; nitriles, monoolefins and conjugated dienes which form a π-complex with M;

n is the number of carbene ligands, where n is at least 1 and the carbene ligands in the complex of the formula I, when n>1, may be the same or different;

m is the number of ligands L, where m may be 0 or ≥1 and the ligands L, when m>1, may be the same or different;

q is the number of ligands K, where q may be 0 or ≥1 and the ligands K, when q>1, may be the same or different, where the sum of n+m+q depends upon the oxidation state and coordination number of the metal atom used and upon the denticity and the charge of the ligands, with the condition that n is at least 1;

Do is a donor atom selected from the group consisting of N, O and S;

r is 1 when Do is N and O when Do is O or S;

$Y^1$, $Y^2$ are each independently hydrogen, alkyl, alkenyl, alkynyl, aryl or heteroaryl;

or $Y^1$ and $Y^2$, together with the carbon atoms to which they are bonded, form a six-membered aromatic ring which may comprise one or two nitrogen atoms, and which is optionally fused to a further ring which is optionally fused and optionally comprises heteroatoms;

$Y^3$ is hydrogen or alkyl;

or $Y^3$ and $Y^2$, together with the donor atom Do and the carbon atom to which $Y^2$ is bonded, form a five- or six-membered ring which, apart from the donor atom Do, may also comprise a further heteroatom selected from the group consisting of N, O and S;

A is a bridge having three or four atoms, of which one or two atoms may be heteroatoms and the remaining atoms are carbon atoms, so that the group

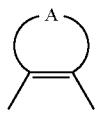

forms a five- or six-membered heteroaromatic ring or benzene ring each of which is optionally substituted by substituents selected from the group consisting of alkyl, alkyloxy, alkylthio, aryl, aryloxy, arylthio, halogen, CN, CHO, alkylcarbonyl, arylcarbonyl, carboxyl, alkyloxycarbonyl, aryloxycarbonyl, hydroxysulfonyl, alkylosysulfonyl, aryloxysulfonyl, $NO_2$ and NO, and optionally fused with a further ring which is optionally fused and optionally comprises heteroatoms, where $Y^1$, together with a group selected from chemical single bond, $C(Y^4)_2$, C(O), O, S, S(O), $SO_2$ and $NY^5$, may optionally form a two-membered bridge B to that carbon atom or heteroatom of the bridge A which is in the α-position to the carbon atom which is bonded to the nitrogen atom of the carbene unit of the carbene ligand;

$Y^4$, $Y^5$ are each independently hydrogen, alkyl, aryl or heteroaryl, and the two $Y^4$ groups in the $C(Y^4)_2$ bridge may be varied independently of one another.

The preferred structural features of the complexes and the preferred definitions of the variables with regard to the use in OLEDs also apply to the complexes claimed in accordance with the invention.

Preferred inventive complexes of the formula I comprise one or more carbene ligands which are obtained by combination of substructures selected from the group of

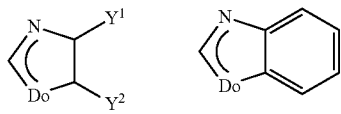

$Y^1, Y^2 =$ hydrogen, alkyl

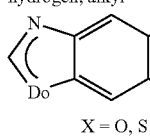

X = O, S

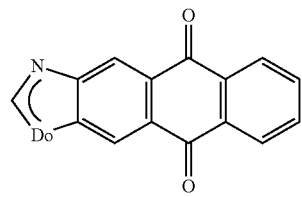

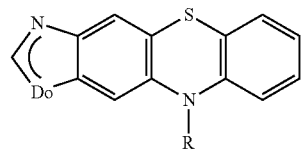

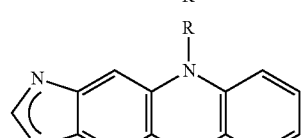

R = hydrogen, alkyl, aryl and selected from the group of

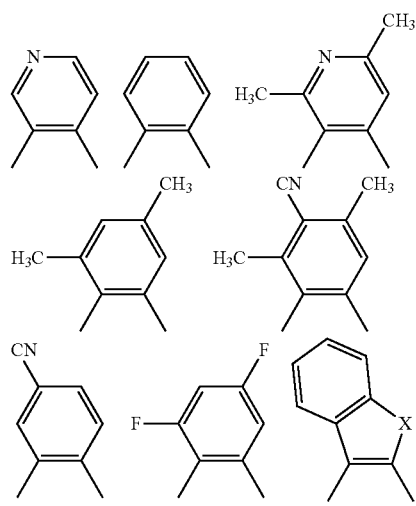

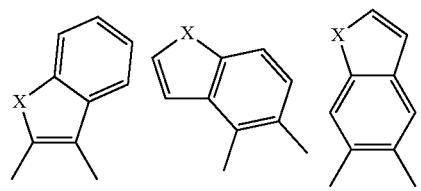

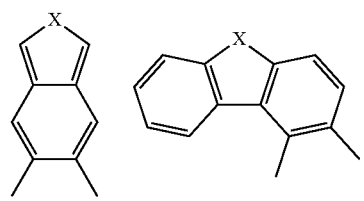

-continued

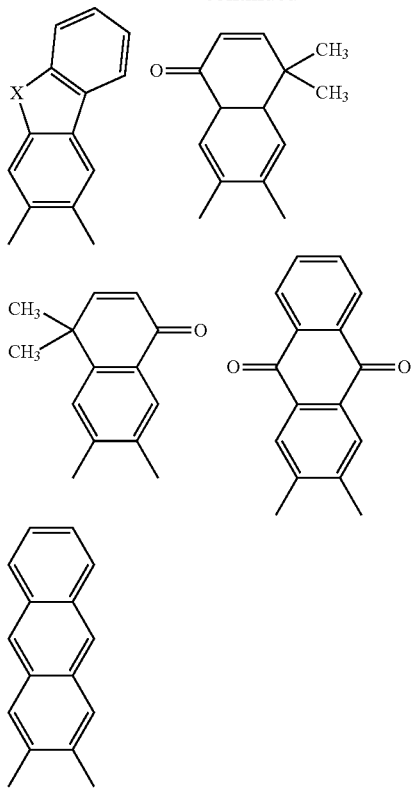

X = O, S, NR; R = hydrogen or alkyl where the donor atom Do is preferably S or N—Y$^3$, and Y$^3$ is preferably methyl, ethyl, n-propyl, isopropyl or tert-butyl.

Particularly preferred inventive complexes of the formula I comprise one or more carbene ligands which are obtained by combination of substructures selected from the group of

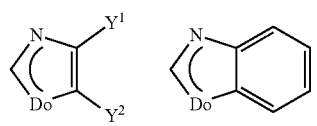

Y$^1$, Y$^2$ = hydrogen, alkyl and selected from the group of

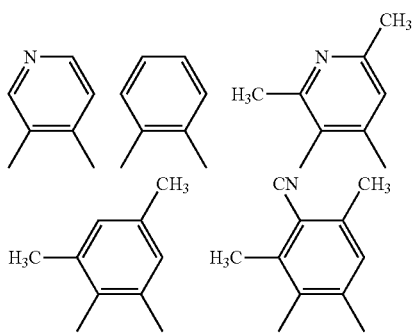

-continued

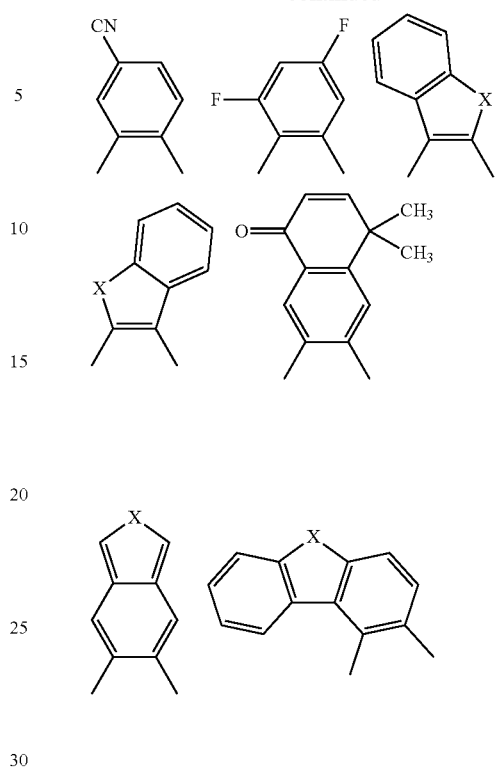

X = O, S, NR; R = hydrogen or alkyl where the donor atom Do is preferably S or N—Y$^3$ and Y$^3$ is preferably methyl, ethyl, n-propyl, isopropyl or tert-butyl.

In particular, the following complexes which have only carbene ligands should be mentioned for this combination:

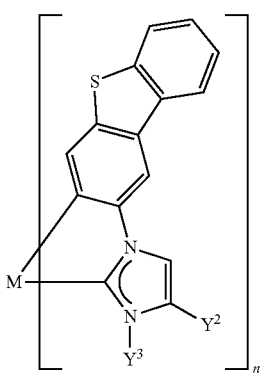

-continued
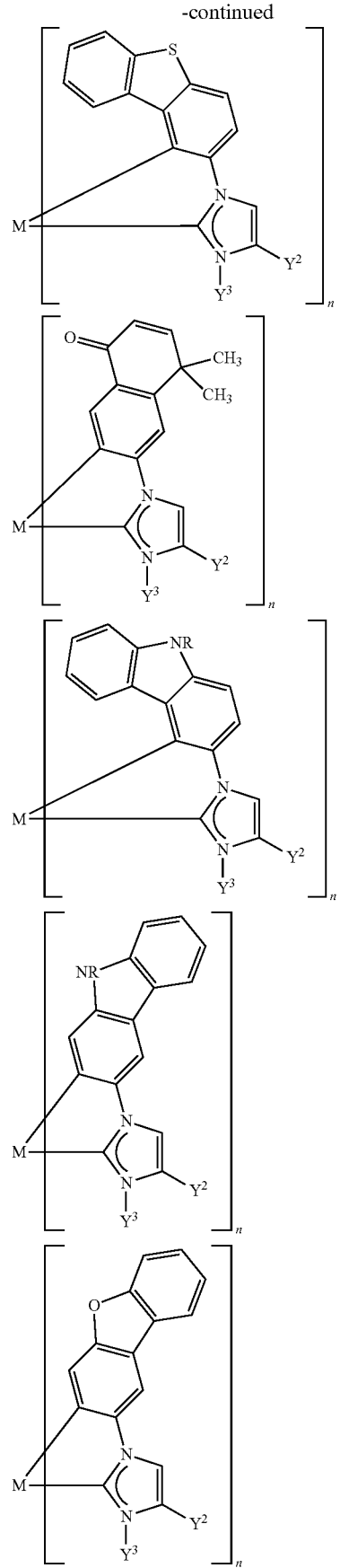
-continued
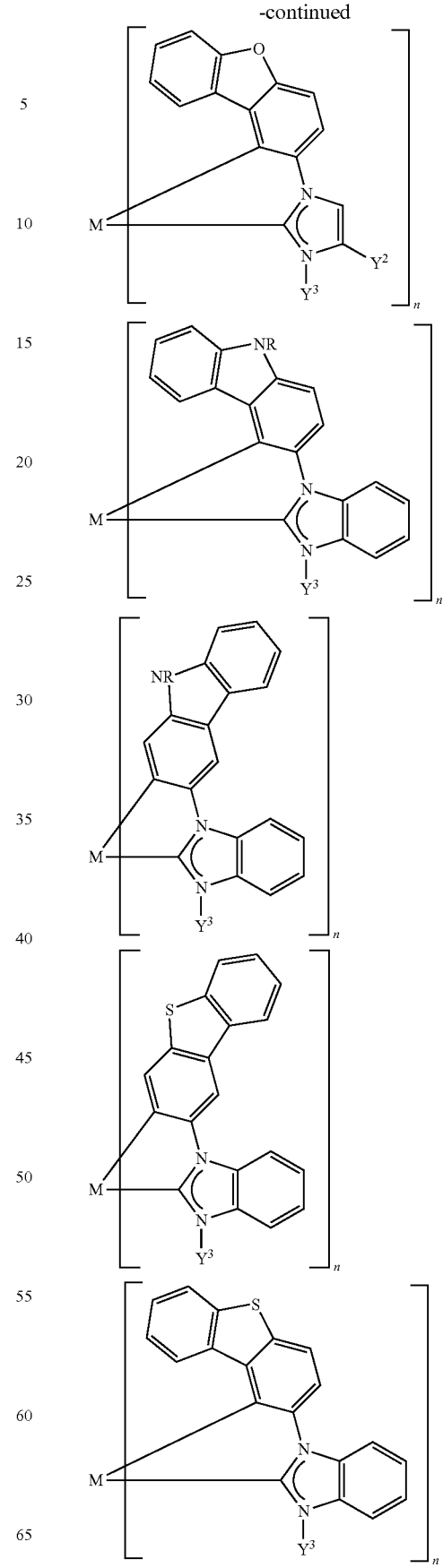

-continued
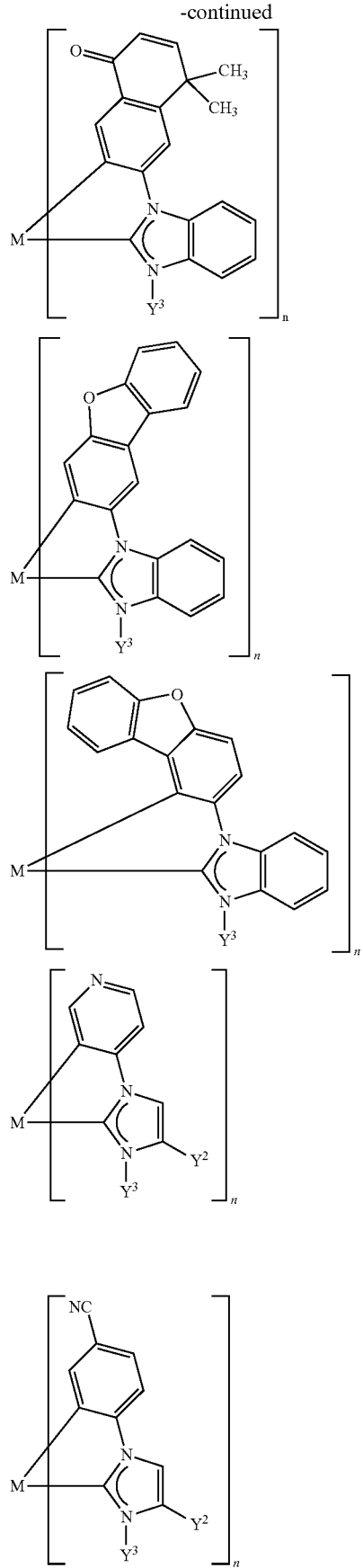
-continued
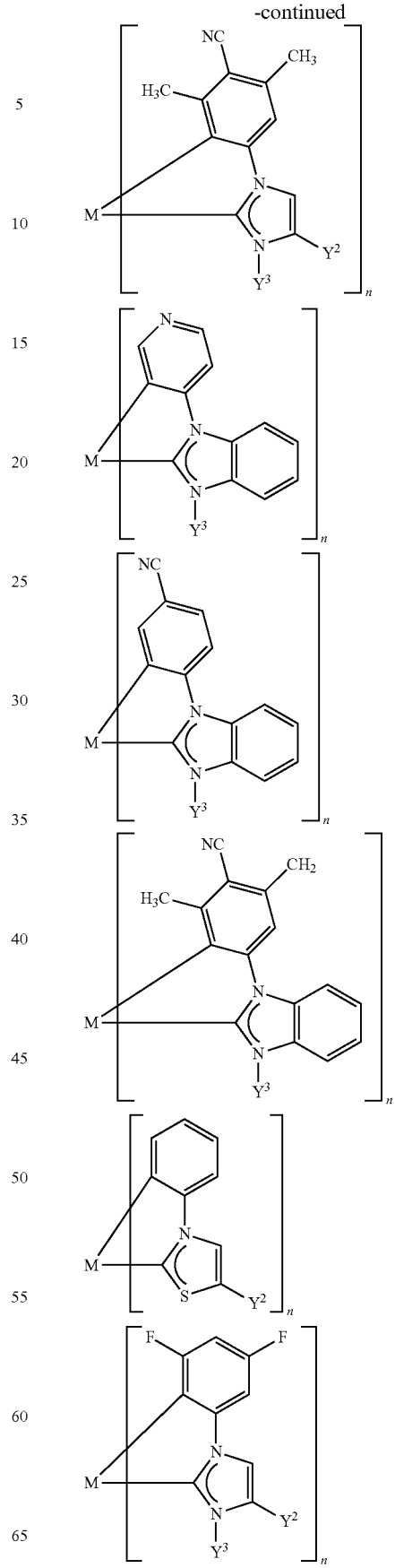

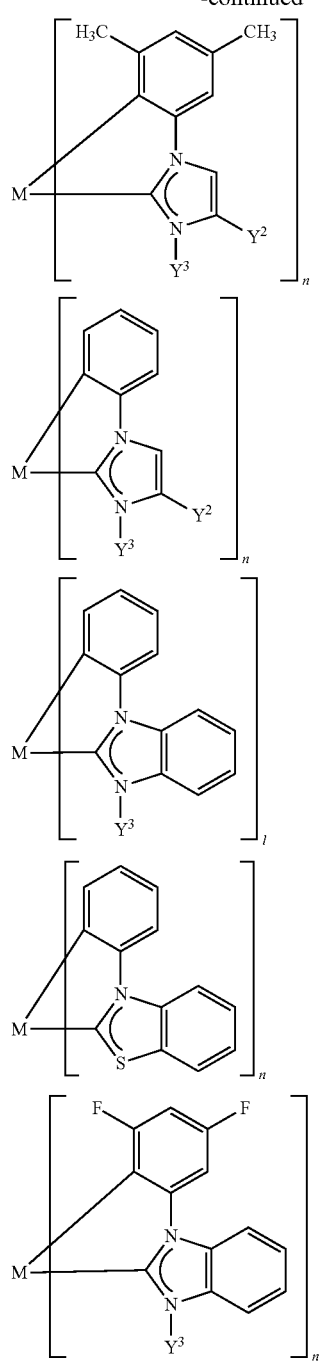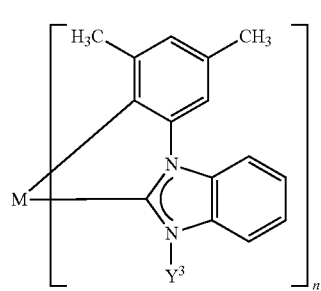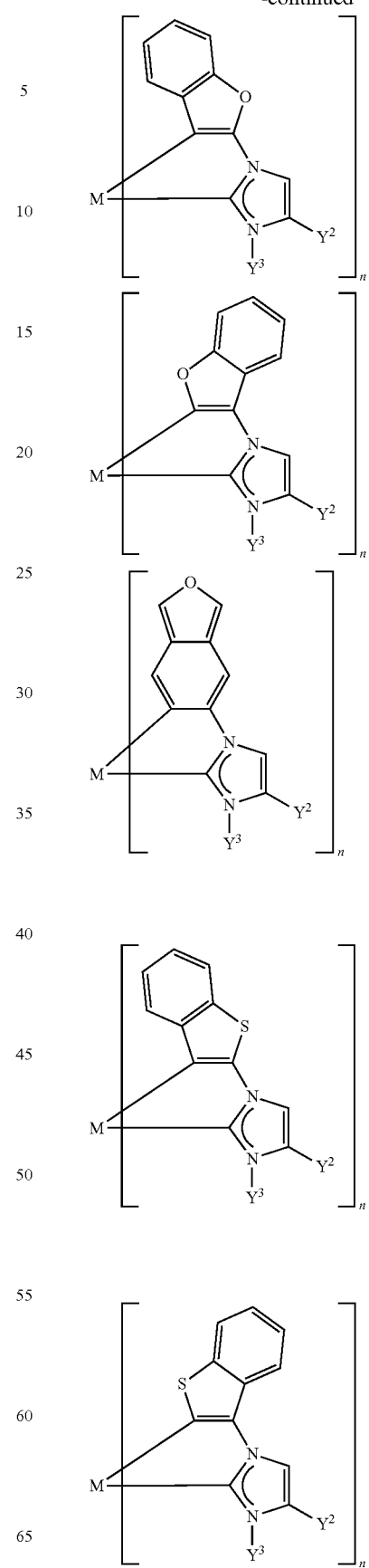

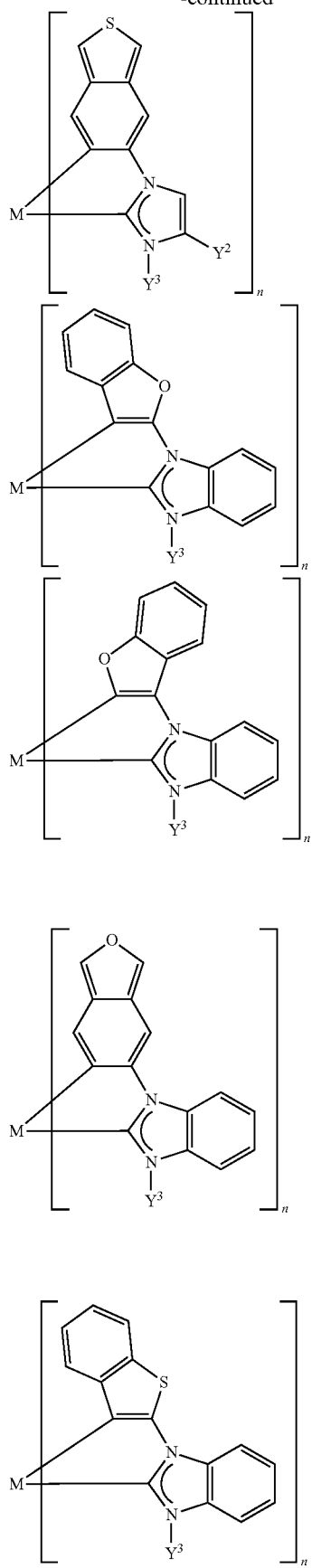
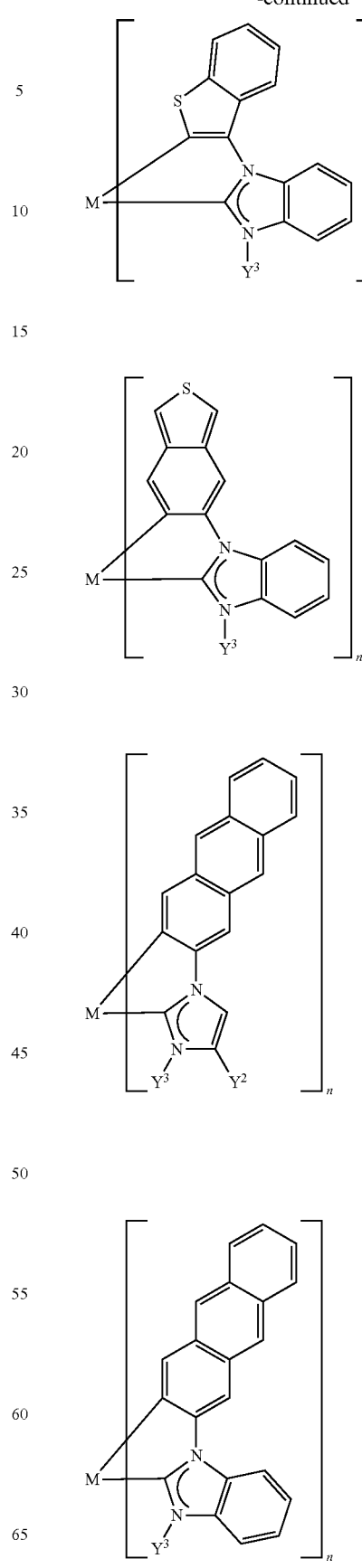

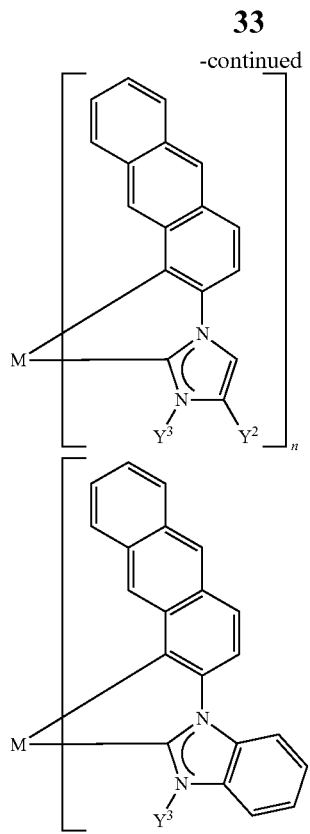

where M is Ru(III), Rh(III), Ir(III), Pd(III) or Pt(II), n is 3 for Ru(III), Rh(III) and Ir(III) and is 2 for Pd(II) and Pt(II), and $Y^2$ and $Y^3$ are each hydrogen, methyl, ethyl, n-propyl, isopropyl or tert-butyl. M is preferably Ir(III) where n=3. $Y^3$ is preferably methyl, ethyl, n-propyl, isopropyl or tert-butyl. Some of the isomeric compounds listed above are shown in order to illustrate what was stated at the outset with regard to the isomerism of the carbene complexes of the formula I.

Further particularly preferred inventive complexes of the formula I comprise one or more carbene ligands which are obtained by combination of substructures selected from the group of

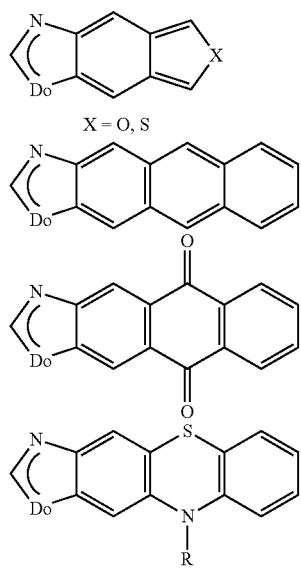

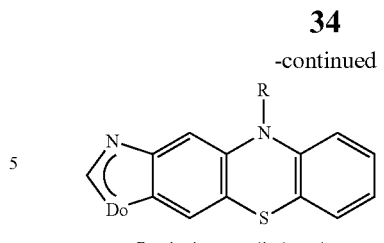

R = hydrogen, alkyl, aryl and selected from the group of

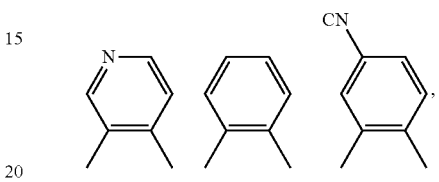

where the donor atom Do is preferably S or N—$Y^3$ and $Y^3$ is preferably methyl, ethyl, n-propyl, isopropyl or tert-butyl.

In particular, the following complexes which have only carbene ligands should be mentioned for this combination:

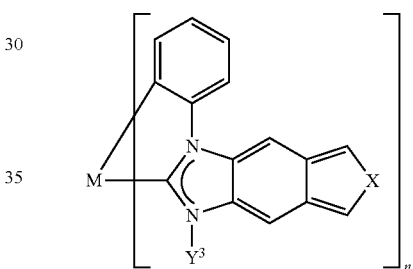

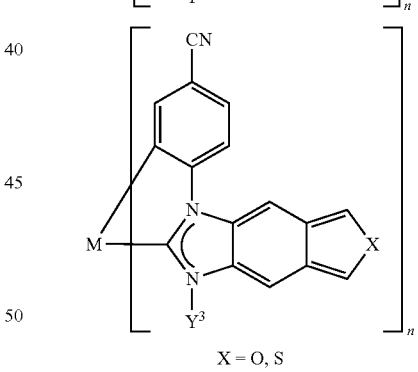

X = O, S

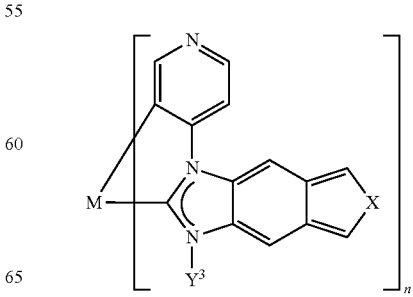

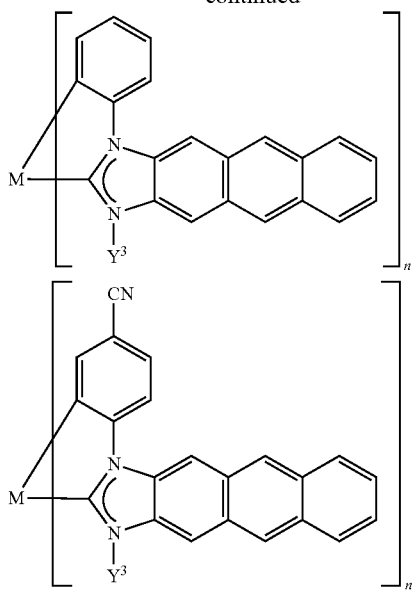
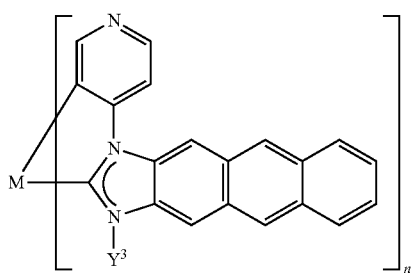
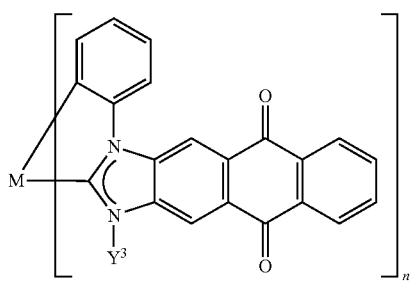
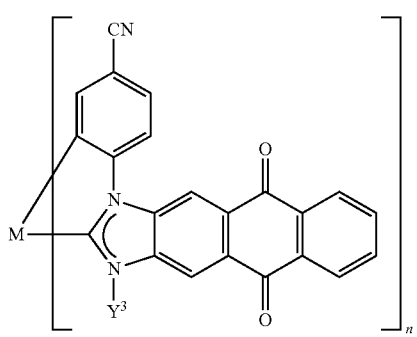

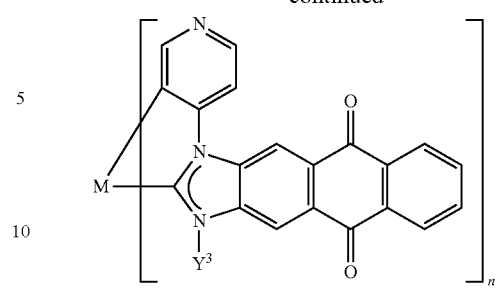

where M is Ru(III), Rh(III), Ir(III), Pd(II) or Pt(II), n is 3 for Ru(III), Rh(III) and Ir(III) and is 2 for Pd(II) and Pt(II), and $Y^3$ is hydrogen, methyl, ethyl, n-propyl, isopropyl or tert-butyl. M is preferably Ir(III) where n=3. $Y^3$ is preferably methyl, ethyl, n-propyl, isopropyl or tert-butyl.

Further particularly preferred inventive complexes of the formula I comprise one or more carbene ligands which comprise substructures selected from the group of:

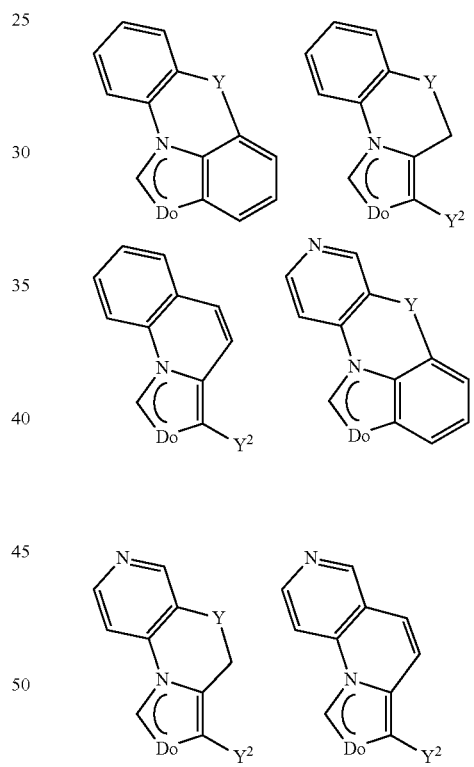
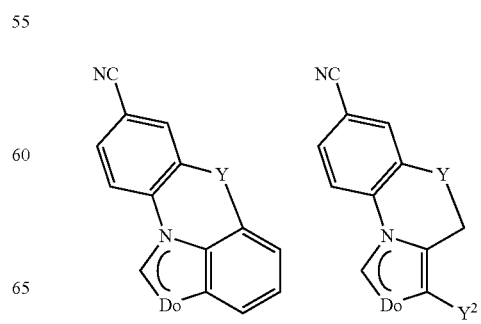

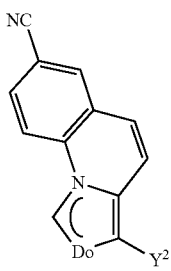

where Do is defined as S or N—Y³ and Y is defined as O, S, C(CH₃)₂ or SO₂, Y² is defined as hydrogen, methyl, ethyl, n-propyl, isopropyl or tert-butyl, and Y³ is defined as methyl, ethyl, n-propyl, isopropyl or tert-butyl.

In particular, corresponding complexes which should be mentioned are:

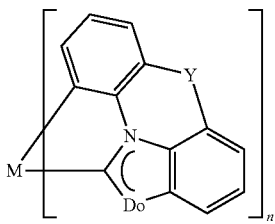
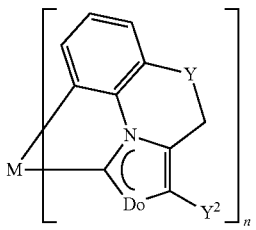
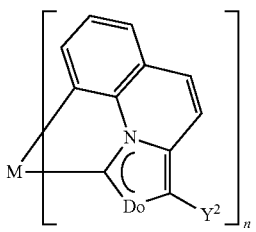
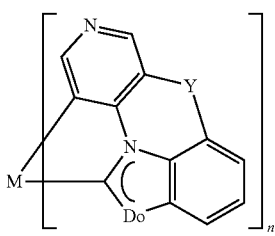
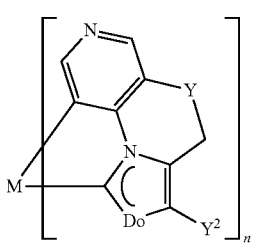

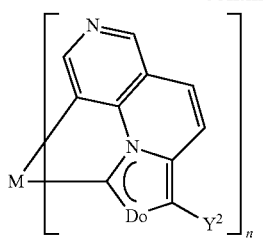
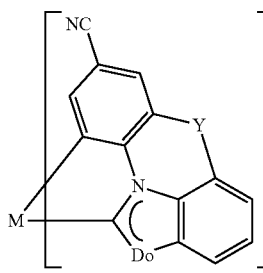
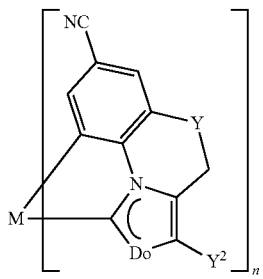
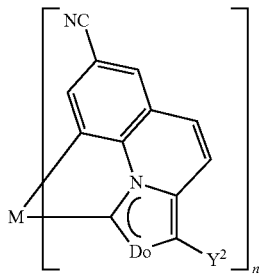
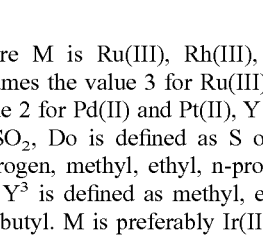

where M is Ru(III), Rh(III), Ir(III), Pd(II) or Pt(II), n assumes the value 3 for Ru(III), Rh(III) and Ir(III) and the value 2 for Pd(II) and Pt(II), Y is defined as O, S, C(CH₃)₂ of SO₂, Do is defined as S or N—Y³, Y² is defined as hydrogen, methyl, ethyl, n-propyl, isopropyl or tert-butyl, and Y³ is defined as methyl, ethyl, n-propyl, isopropyl or tert-butyl. M is preferably Ir(III) where n=3.

Examples which should be mentioned are:

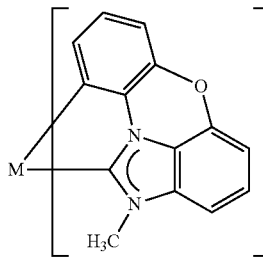

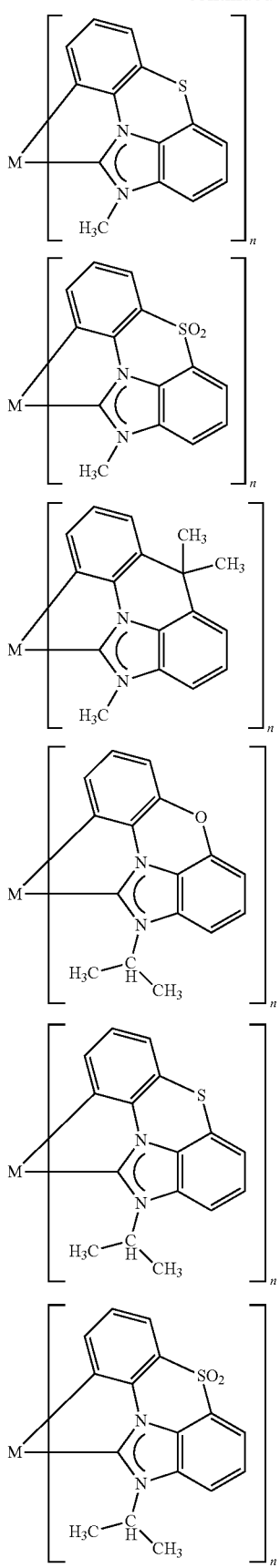

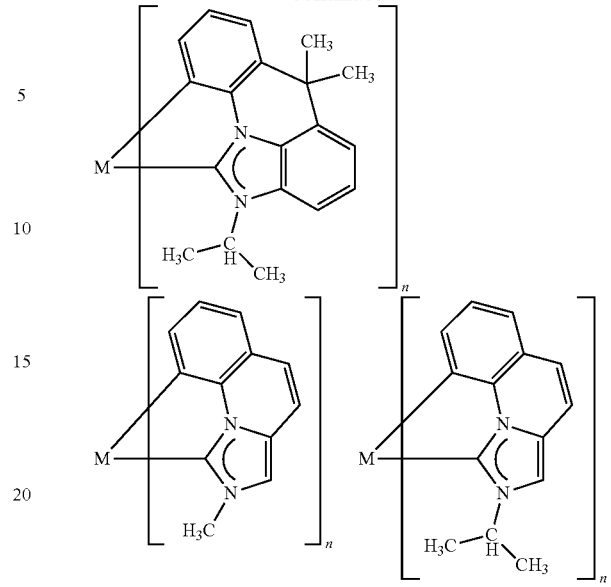

where M is Ru(III), Rh(III) and in particular Ir(III), Pd(II) or Pt(II), n assumes the value of 3 for Ru(III), Rh(III) and Ir(III), and the value of 2 for Pd(II) and Pt(II).

Further preferred inventive complexes of the formula I comprise one or more carbene ligands which are obtained by combination of substructures selected from the group of

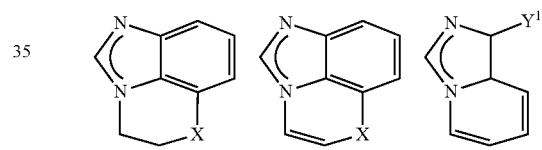

where X is a $CH_2$ group or an oxygen atom and $Y^1$ is hydrogen, methyl, ethyl, isopropyl or tert-butyl,
and selected from the group of

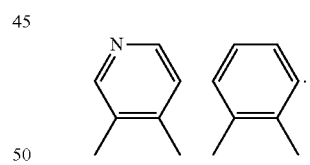

In particular, the following complexes which have only carbene ligands should be mentioned for this combination.

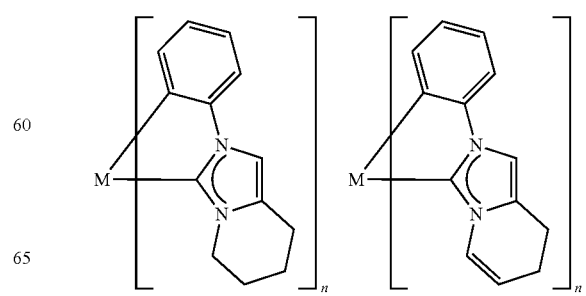

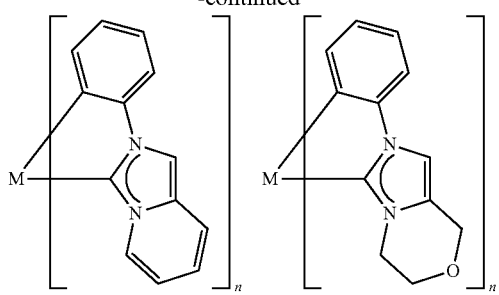
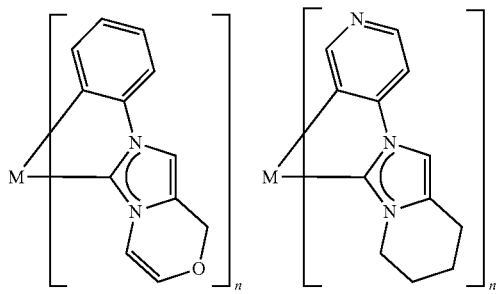
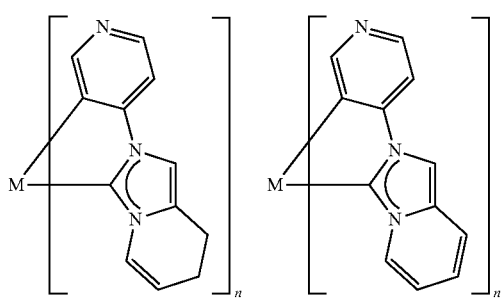
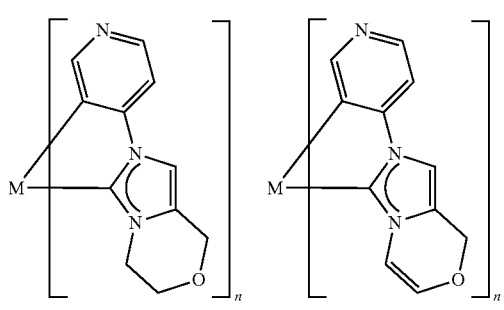
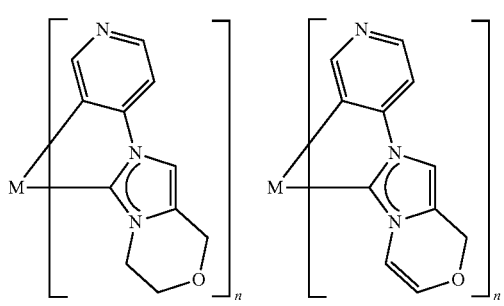
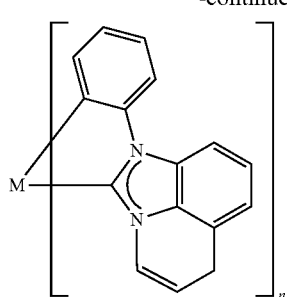
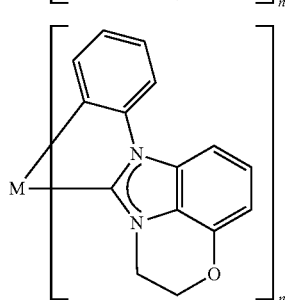
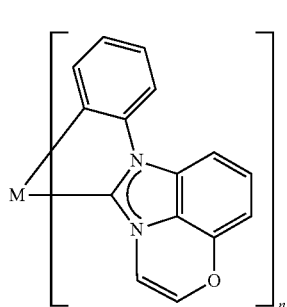
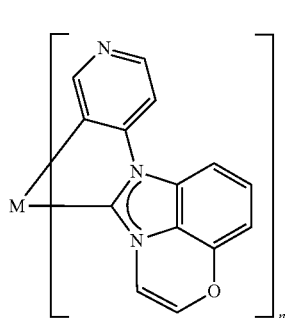

-continued

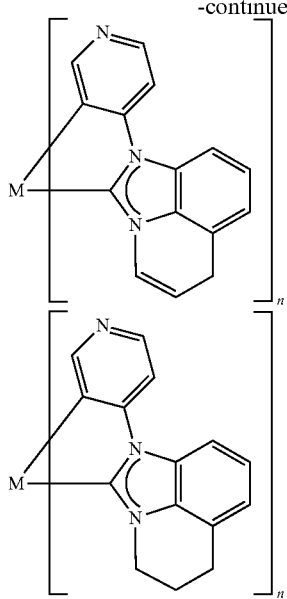

where M is Ru(III), Rh(III) and in particular Ir(III), Pd(II) or Pt(II), n assumes the value of 3 for Ru(III), Rh(III) and Ir(III), and assumes the value of 2 for Pd(II) and Pt(II).

Although the attention has been directed in the preceding remarks to complexes having the same carbene ligands, it should be noted here that complexes having different carbene ligands and/or having ligands L and/or K (corresponding ligands L and K have already been defined at the outset) may of course also find use in accordance with the invention.

With reference to the table below, the complexes having trivalent metal centers ML'(L")$_2$ with two different carbene ligands L' and L" are specified schematically

| L' | L" |
|---|---|
| L$^1$ | L$^2$ |
| L$^1$ | L$^3$ |
| L$^1$ | L$^4$ |
| L$^1$ | L$^5$ |
| L$^1$ | L$^6$ |
| L$^1$ | L$^7$ |
| L$^2$ | L$^3$ |
| L$^2$ | L$^4$ |
| L$^2$ | L$^5$ |
| L$^2$ | L$^6$ |
| L$^2$ | L$^7$ |
| L$^3$ | L$^4$ |
| L$^3$ | L$^5$ |
| L$^3$ | L$^6$ |
| L$^3$ | L$^7$ |
| L$^4$ | L$^5$ |
| L$^4$ | L$^6$ |
| L$^4$ | L$^7$ |
| L$^5$ | L$^6$ |
| L$^5$ | L$^7$ |
| L$^6$ | L$^7$ |
| L$^7$ | L$^6$ |
| L$^7$ | L$^5$ |
| L$^7$ | L$^4$ |
| L$^7$ | L$^3$ |
| L$^7$ | L$^2$ |
| L$^7$ | L$^1$ |
| L$^6$ | L$^5$ |
| L$^6$ | L$^4$ |
| L$^6$ | L$^3$ |
| L$^6$ | L$^2$ |
| L$^6$ | L$^1$ |
| L$^5$ | L$^4$ |
| L$^5$ | L$^3$ |
| L$^5$ | L$^2$ |
| L$^5$ | L$^1$ |
| L$^4$ | L$^3$ |
| L$^4$ | L$^2$ |
| L$^4$ | L$^1$ |
| L$^3$ | L$^2$ |
| L$^3$ | L$^1$ |
| L$^2$ | L$^1$ | where M is, for example, Ru(III), Rh(III) or Ir(III), in particular Ir(III), and L' and L" are, for example, ligands selected from the group of the ligands L$^1$ to L$^7$ L$^1$
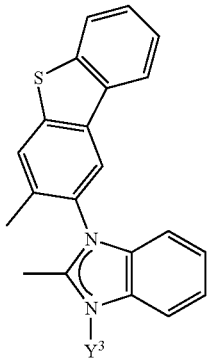

L$^2$
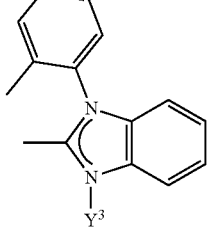

L$^3$
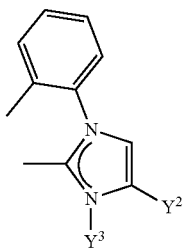

L$^4$
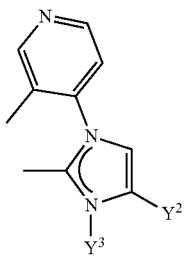

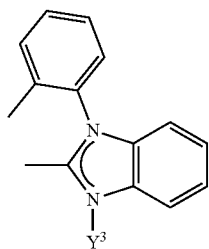

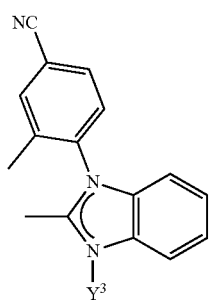

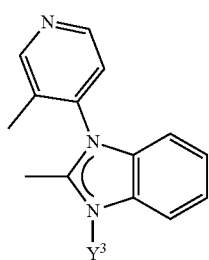

$Y^2$ is hydrogen, methyl, ethyl, n-propyl, isopropyl or tert-butyl, and $Y^3$ is methyl, ethyl, n-propyl, isopropyl or tert-butyl.

One representative of these complexes having different carbene ligands ($L'=L^4$ where $Y^2$=hydrogen and $Y^3$=methyl; $L''=L^2$ where $Y^2$=hydrogen and $Y^3$=methyl) is, for example:

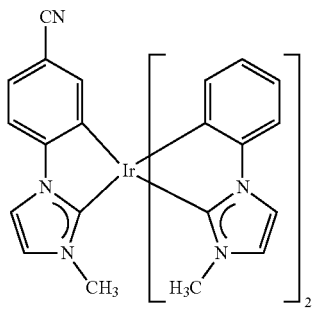

It will be appreciated that all three carbene ligands in the complexes, used in accordance with the invention, of trivalent metal centers (for instance in the case of Ru(III), Rh(III) or Ir(III)) may also be different from one another.

Examples of complexes of trivalent metal centers M having ligands L (here monoanionic, bidentate ligands) as "spectator ligands" are LML'L", LM(L')$_2$ and L$_2$ML', in which M is, for instance, Ru(III), Rh(III) or Ir(III), in particular Ir(III), and L' and L" are each as defined above. For the combination of L' and L" in the complexes LML'L", this results in:

| L'  | L"  |
|-----|-----|
| L¹  | L²  |
| L¹  | L³  |
| L¹  | L⁴  |
| L¹  | L⁵  |
| L¹  | L⁶  |
| L¹  | L⁷  |
| L²  | L³  |
| L²  | L⁴  |
| L²  | L⁵  |
| L²  | L⁶  |
| L²  | L⁷  |
| L³  | L⁴  |
| L³  | L⁵  |
| L³  | L⁶  |
| L³  | L⁷  |
| L⁴  | L⁵  |
| L⁴  | L⁶  |
| L⁴  | L⁷  |
| L⁵  | L⁶  |
| L⁵  | L⁷  |
| L⁶  | L⁷  |

Possible ligands L are in particular acetylacetonate and derivatives thereof, picolinate, Schiff bases, amino acids, tetrakis(1-pyrazolyl)borates and the bidentate monoanionic ligands specified in WO 02/15645; in particular, acetylacetonate and picolinate are of interest. In the case of the complexes L$_2$ML', the ligands L may be the same or different.

One representative of these complexes having different carbene ligands ($L'=L^4$ where $Y^2$=hydrogen and $Y^3$=methyl; $L''=L^2$ where $Y^2$=hydrogen and $Y^3$=methyl) is, for example:

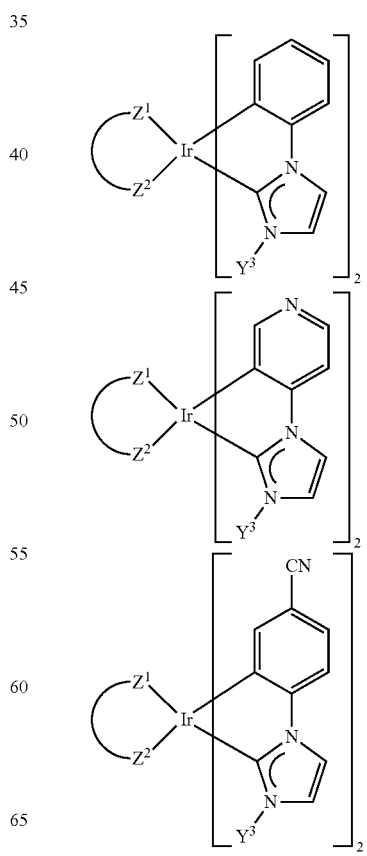

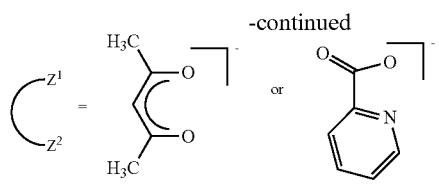

where $z^1$ and $z^2$ in the symbol

represent the two "teeth" of the ligand L. $Y^3$ is hydrogen, methyl, ethyl, n-propyl, isopropyl or tert-butyl, in particular methyl, ethyl, n-propyl or isopropyl.

The aforementioned uncharged transition metal complexes are outstandingly suitable as emitter molecules in organic light-emitting diodes (OLEDs). Simple variations of the ligands or of the central metal make it possible to provide transition metal complexes which exhibit the electroluminescence in the red, green and in particular in the blue region of the electromagnetic spectrum. Uncharged transition metal complexes used in accordance with the invention are therefore suitable for use in industrially usable full color displays.

In addition, the aforementioned uncharged transition metal complexes are suitable as electron, exciton or hole blockers in OLEDs, depending upon the ligands used and the central metal used.

The inventive transition metal-carbene complexes of the formula I may be prepared analogously to the processes known to those skilled in the art. Suitable preparation processes are detailed, for example, in the review articles W. A. Hermann et al., Advances in Organometallic Chemistry, Vol. 48, 1 to 69, W. A. Hermann et al., Angew. Chem. 1997, 109, 2256 to 2282 and G. Bertrand et al. Chem. Rev. 2000, 100, 39 to 91 and the literature cited therein.

The present application further provides a process for preparing the carbene complex of the formula I.

In the process according to the invention, the inventive transition metal complexes of the formula I are prepared by deprotonating the ligand precursors corresponding to the particular carbene ligands and subsequently or simultaneously reacting with suitable metal complexes comprising the desired metal.

In addition, it is possible to prepare the inventive transition metal complexes by direct use of Wanzlick olefins.

Suitable ligand precursors are known to those skilled in the art. They are preferably cationic precursors having negatively charged counterions.

In one embodiment, the cationic precursors are reacted with a base, and the intermediates formed may be different depending upon the precursor. Depending on the reaction, what are formed are, for example, alkoxide derivatives, dimeric Wanzlick olefins or the free N-heterocycle carbenes. Alkoxide derivatives and Wanzlick olefins are typically thermally stressed in the presence of a suitable metal precursor to eliminate the alcohol or to cleave the dimer, and the metal-carbene compound is formed in the presence of suitable metal complexes. The reactions are typically carried out in suitable solvents which are known to those skilled in the art or can be determined by simple preliminary experiments, and it is possible in the case of two-stage variants to use the same solvent or different solvents for the two steps. Possible solvents available for selection are, for example, aromatic and aliphatic solvents or ethers, for example toluene, tetrahydrofuran, and additionally alcohols or chlorinated hydrocarbons such as methylene chloride, liquid ammonia, if appropriate in a mixture with tetrahydrofuran, and polar-aprotic solvents, for instance dimethylformamide, N-methylpyrrolidone or acetonitrile. Alcohols and halogenated hydrocarbons are generally used only when no free carbene is formed in the reaction.

The base for the reaction with the ligand precursors may be present in the metal compounds which comprise the desired metal M of the complexes of the formula I. Possible metal compounds are metal acetates, metal acetylacetonates, metal amides or metal alkoxylates. In addition, the reaction may be effected with external bases such as KO$^t$Bu, NaO$^t$Bu, LiO$^t$Bu, NaH, disilazides and phosphazene bases. It is also possible to carry out the reaction with the ligand precursors using the metal compounds comprising the base in combination with external bases.

The inventive transition metal-carbene complexes of the formula I are preferably obtained starting from the corresponding cationic precursors selected from the group consisting of azolium salts, in particular imidazolium salts, benzimidazolium salts; triazolium salts and azolidinium salts, in particular imidazolidinium salts, by reacting with an external base, preferably KO$^t$Bu or disilazides, in particular, for example, potassium bis(trimethylsilyl)amide, and subsequent or in situ reaction of the resulting intermediate with a complex of the desired metal.

Suitable complexes of the desired metal are known to those skilled in the art. The desired metal in the metal complex used and the corresponding metal of the transition metal-carbene complex I prepared therefrom do not have to have the same oxidation state.

In the preparation of iridium(III) complexes of the general formula I which are particularly preferred according to the present application, it is possible, for example, to use the following iridium(III) complexes: [(μ-Cl)Ir(η$^4$-1,5-cod)]$_2$, [(μ-Cl)Ir(η$^2$-1,5-coe)$_2$]$_2$, Ir(acac)$_3$, IrCl$_3$.n H$_2$O, (tht)$_3$IrCl$_3$, where cod is cyclooctadiene, coe is cyclooctene, acac is acetylacetonate and tht is tetrahydrothiophene.

Alkoxide derivatives or Wanzlick olefins are typically added at room temperature to the appropriate metal precursors and subsequently thermally stressed, in the course of which the corresponding alcohol is eliminated in the case of the alkoxide derivatives, or the dimeric Wanzlick olefins are cleaved, and the metal-carbene compound is formed. Typically, these reactions take place at temperatures of from 20 to 160° C. When the intermediates used are to be free carbenes (e.g. imidazolin-2-ylidenes), they are generally added to the metal precursor with cooling, subsequently warmed to room temperature (20 to 25° C.) and/or if appropriate to even higher temperature. Typically, the reaction is carried out within a temperature range of from −78 to +160° C.

The ratio of metal complex used to ligand precursor used is dependent upon the desired complex which bears at least two carbene ligands. When the metal atom is Ir(III), which is particularly preferred, and the desired transition metal complex comprises three carbene ligands, which is likewise particularly preferred, the molar amount of ligand precursors has to be about three times as large as the molar amount of metal in the metal complex, and a small excess of the ligand precursor may be used.

The molar ratio of metal in the metal complex to the molar amount of ligand precursors is generally from 1:3 to 1:6.

The molar ratio of base used to ligand precursor used is typically from 3:1 to 1:1, preferably from 2:1 to 1:1. When strong bases, such as LiO$^t$Bu, NaO$^t$Bu, KO$^t$Bu or potassium bis(trimethylsilyl)amide (KHMDS) are used, a molar ratio of base to ligand precursor of 1:1 is generally sufficient.

The preparation of two inventive iridium complexes having N-heterocyclic carbene ligands is shown below by way of example:

Imidazolinylidene Complex:

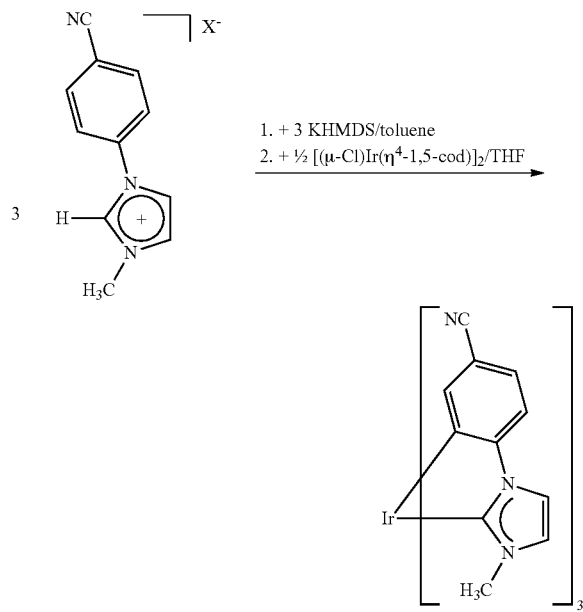

$X^-$ is an anionic group, preferably a halide, pseudohalide or another monoanionic group, for example $Cl^-$, $Br^-$, $I^-$, $BF_4^-$, $PF_6^-$, $CN^-$, $SCN^-$, more preferably $BF_4^-$, $PF_6^-$.

Benzimidazolinylidene Complex:

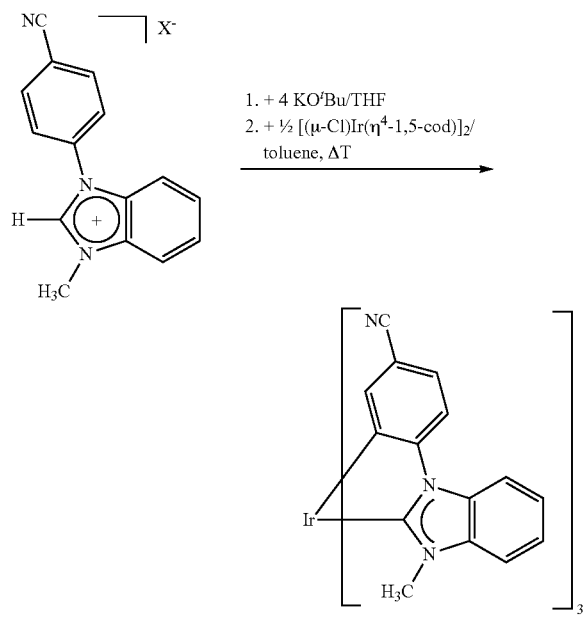

$X^-$ has already been defined above.

The transition metal-carbene complexes used in accordance with the invention are outstandingly suitable as emitter substances, since they have an emission (electroluminescence) in the visible region of the electromagnetic spectrum. With the aid of the transition metal-carbene complexes used in accordance with the invention as emitter substances, it is possible to provide compounds which have electroluminescence in the red, green and in the blue region of the electromagnetic spectrum. It is thus possible with the aid of the transition metal-carbene complexes used in accordance with the invention as emitter substances to provide industrially usable full color displays.

The availability of differently substituted carbene ligands and different transition metals makes it possible to prepare emitter substances which emit light in different regions of the electromagnetic spectrum. For these substances, the quantum yield is high and the stability of the transition metal-carbene complexes in the device, especially those having N-heterocyclic carbene ligands, is high.

In addition, the aforementioned uncharged transition metal complexes are suitable as electron, exciton or hole blockers in OLEDs, depending on the ligands used and the central metal used.

Organic light-emitting diodes are in principle composed of several layers:
1. Anode
2. Hole-transporting layer
3. Light-emitting layer
4. Electron-transporting layer
5. Cathode However, it is also possible that the OLED does not have all of the layers mentioned; for example an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5), or the layers (1), (3), (4) and (5), are likewise suitable.

The transition metal-carbene complexes according to the present application may be used in various layers of an OLED. The present invention therefore further provides an OLED comprising at least one transition metal-carbene complex according to the present application. The transition metal-carbene complexes are used preferably as emitter molecules in the light-emitting layer. The present invention therefore further provides a light-emitting layer comprising at least one transition metal-carbene complex as an emitter molecule. Preferred transition metal-carbene complexes, in particular transition metal-carbene complexes having N-heterocyclic carbene ligands, have already been specified above.

The inventive transition metal-carbene complexes, or those used in accordance with the invention, may be present in bulk, without further additives, in the light-emitting layer or another layer of the OLED, preferably in the light-emitting layer. However, it is likewise possible that, in addition to the transition metal-carbene complexes used in accordance with the invention, further compounds are present in the layers comprising at least one transition metal-carbene complex according to the present application, preferably in the light-emitting layer. For example, a fluorescent dye may be present in the light-emitting layer in order to alter the emission color of the transition metal-carbene complex used as an emitter molecule. In addition, a diluent material may be used. This diluent material may be a polymer, for example poly(N-vinylcarbazole) or polysilane. However, the diluent material may likewise be a small molecule, for example 4, 4'-N,N'-dicarbazolebiphenyl (CDP=CBP) or tertiary aromatic amines. When a diluent material is used, the proportion of the transition metal-carbene complexes used in accordance with the invention in the light-emitting layer is generally less than 60% by weight, preferably less than 50% by weight, more preferably from 5 to 40% by weight.

The individual aforementioned layers of the OLED may be composed of 2 or more layers. For example, the hole-transporting layer may be composed of one layer into which holes are injected from the electrode and one layer which transports the holes from the hole-injecting layer away into the light-emitting layer. The electron-transporting layer may likewise consist of a plurality of layers, for example one layer in which electrons are injected by the electrode and one layer which receives electrons from the electron-injecting layer and transports them into the light-emitting layer. These specified layers are each selected according to factors such as energy level, thermal resistance and charge carrier mobility, and also energy differential of the layers mentioned with the organic layers or the metal electrodes. Those skilled in the art are capable of selecting the structure of the OLEDs in such a way that it is adapted optimally to the transition metal-carbene complexes used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer aligned to the work function of the cathode.

The present application further provides an OLED comprising at least one inventive light-emitting layer. The further layers in the OLED may be composed of any material which is typically used in such layers and is known to those skilled in the art.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to omit the light formed.

Suitable hole-transporting materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transporting material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl)](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4',4',4"-tris(N,N-diphenylamino)triphenylamine (TDTA) and porphyrin compounds, and also phthalocyanines such as copper phthalocyanines.

Customarily used hole-transporting polymers are selected from the group consisting of polyvinylcarbazoles, (phenylmethyl)polysilanes, PEDoT (poly(3,4-ethylenedioxythiophene)), preferably PEDoT doped with PSS (polystyrene sulfonate), and polyanilines. It is likewise possible to obtain hole-transporting polymers by doping hole-transporting molecules into polymers such as polystyrene and polycarbonate. Suitable hole-transporting molecules are the molecules already mentioned above.

Suitable electron-transporting materials for the layer (4) of the inventive OLEDs comprise metals chelated with oxinoid compounds, such as tris(8-quinolinolato)-aluminum ($Alq_3$), compounds based on phenanthroline such as 2,9-dimethyl-4,7-diphenyl-1,10-phenanthroline (DDPA=BCP) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole-transporting materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole-transporting materials may be doped with electron acceptors; for example, phthalocyanines or arylamines such as TPD or TDTA may be doped with tetrafluorotetracyanoquinodimethane (F4-TCNQ). The electron-transporting materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. Suitable materials for the cathode are selected from the group consisting of alkali metals of group 1, for example Li, Cs, alkaline earth metals of group 2, for example calcium, barium or magnesium, metals of group 12 of the Periodic Table of the Elements, comprising the lanthanides and actinides, for example samarium. In addition, metals such as aluminum or indium, and combinations of all of the metals mentioned, may also be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
 a hole injection layer between the anode (1) and the hole-transporting layer (2);
 a blocking layer for electrons and/or excitons between the hole-transporting layer (2) and the light-emitting layer (3);
 a blocking layer for holes and/or excitons between the light-emitting layer (3) and the electron-transporting layer (4);
 an electron injection layer between the electron-transporting layer (4) and the cathode (5).

However, it is also possible that the OLED does not have all of the layers (1) to (5) mentioned; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers are known to those skilled in the art and disclosed, for example, in WO 00/70655.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency and lifespan.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed. Compositions which, in addition to the at least one inventive transition metal-carbene complex, have a polymeric material in one of the layers of the OLED, preferably in the light-emitting layer, are generally applied as a layer by means of solution-mediated processes.

In general, the different layers have the following thicknesses: anode (1) from 500 to 5000 Å, preferably from 1000 to 2000 Å; hole-transporting layer (2) from 50 to 1000 Å, preferably from 200 to 800 Å; light-emitting layer (3) from 10 to 1000 Å, preferably from 100 to 800 Å; electron-transporting layer (4) from 50 to 1000 Å, preferably from 200 to 800 Å; cathode (5) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the transition metal-carbene complexes used in accordance with the invention in at least one layer of the OLED, preferably as emitter molecules in the light-emitting layer of the inventive OLEDs, allows OLEDs having a high efficiency to be obtained. The efficiency of the inventive OLEDs may additionally be improved by optimizing the other layers. For example, highly efficient cathodes such as Ca or Ba, if appropriate in combination with an intermediate layer of LiF, may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to ease electroluminescence.

The inventive OLEDs may be used in all devices in which electroluminescence is useful. Suitable devices are preferably selected from stationary and mobile visual display units (VDUs). Stationary VDUs are, for example, VDUs of computers, televisions, VDUs in printers, kitchen appliances and advertising panels, illuminations and information panels. Mobile VDUs are, for example, VDUs in mobile telephones, laptops, digital cameras, vehicles and destination displays on buses and trains.

In addition, the transition metal-carbene complexes used in accordance with the invention may be used in OLEDs having inverse structure. In these inverse OLEDs, preference is given to using the transition metal-carbene complexes in these inverse OLEDs again in the light-emitting layer. The structure of inverse OLEDs and the materials customarily used therein are known to those skilled in the art.

The above-described inventive transition metal complexes, or those used in accordance with the invention, may, in addition to the use in OLEDs, be used as colorants which emit in the visible region of the electromagnetic spectrum on irradiation by light (photoluminescence). Such colorants are used preferably as colorants in polymeric materials.

The present application therefore further provides for the use of the above-described inventive transition metal-carbene complexes or those used in accordance with the invention for the bulk coloration of polymeric materials.

Suitable polymeric materials are polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene, polyisoprene and the copolymers of the monomers listed.

In addition, the above-described inventive transition metal complexes or those used in accordance with the invention may be used in the following applications:
 Use of the transition metal complexes as or in vat dye(s), for example for coloring natural materials; examples are paper, wood, straw, leather, pelts or natural fiber materials such as cotton, wool, silk, jute, sisal, hemp, flax or animal hairs (for example horsehair) and their conversion products, for example viscose fibers, nitrate silk or copper rayon.

Use of the transition metal complexes as colorants, for example for coloring paints, varnishes and other surface coating compositions, paper inks, printing inks, other inks and other colors for drawing and writing purposes.

Use of the transition metal complexes as pigments, for example for coloring paints, varnishes and other surface coating compositions, paper colors, printing inks, inks and other colors for drawing and writing purposes.

Use of the transition metal complexes as pigments in electrophotography: for example for dry copying systems (Xerox process) and laser printers.

Use of the transition metal complexes for security marking purposes, for which high chemical and photochemical stability and, if appropriate, also the luminescence of the substances is of significance. This is preferably for checks, check cards, banknotes, coupons, documents, identification papers and the like, in which a particular, unmistakable color impression is to be achieved. Also possible are uses against trademark piracy, for example.

Use of the transition metal complexes as an additive to other colors in which a particular shade is to be achieved; preference is given to particularly brilliant colors.

Use of the transition metal complexes for marking articles for machine recognition of these articles using the luminescence, preferably machine recognition of articles for sorting, including, for example, for the recycling of plastics.

Use of the transition metal complexes as luminescent dyes for machine-readable markings; preference is given to alphanumeric markings or barcodes.

Use of the transition metal complexes for adjusting the frequency of light, for example to convert short-wavelength light into longer-wavelength, visible light.

Use of the transition metal complexes in display elements for any kind of display, information and marking purposes, for example in passive display elements, information signs and traffic signs, such as traffic lights.

Use of the transition metal complexes in inkjet printers, preferably in homogeneous solution as luminescent ink.

Use of the transition metal complexes as a starting material for superconductive organic materials.

Use of the transition metal complexes for solid-state luminescent markings.

Use of the transition metal complexes for decorative purposes.

Use of the transition metal complexes for tracer purposes, for example in biochemistry, medicine, engineering and natural sciences. In this use, the dyes can be bonded covalently to substrates or via secondary valences such as hydrogen bonds or hydrophobic interactions (adsorption).

Use of the transition metal complexes as luminescent dyes in high-sensitivity detection methods (cf. C. Aubert, J. Fünfschilling, I. Zschocke-Gränacher and H. Langhals, Z. Analyt. Chem. 320 (1985) 361).

Use of the transition metal complexes as luminescent dyes in scintillation devices.

Use of the transition metal complexes as dyes or luminescent dyes in optical light-collection systems.

Use of the transition metal complexes as dyes or luminescent dyes in luminescent solar collectors (cf. Langhals, Nachr. Chem. Tech. Lab. 28 (1980) 716).

Use of the transition metal complexes as dyes or luminescent dyes in luminescence-activated displays (cf. W. Greubel and G. Baur, Elektronik 26 (1977) 6).

Use of the transition metal complexes as dyes or luminescent dyes in cold light sources for light-induced polymerization for the production of plastics.

Use of the transition metal complexes as dyes or luminescent dyes for materials testing, for example in the production of semiconductor circuits.

Use of the transition metal complexes as dyes or luminescent dyes for the investigation of microstructures of integrated semiconductor components.

Use of the transition metal complexes as dyes or luminescent dyes in photoconductors.

Use of the transition metal complexes as dyes or luminescent dyes in photographic processes.

Use of the transition metal complexes as dyes or luminescent dyes in display, illumination or image conversion systems, in which excitation occurs by means of electrons, ions or UV radiation, for example in luminescent displays, Braun tubes or in fluorescent tubes.

Use of the transition metal complexes as dyes or luminescent dyes as part of an integrated semiconductor circuit, the dyes being used as such or in conjunction with other semiconductors, for example in the form of epitaxy.

Use of the transition metal complexes as dyes or luminescent dyes in chemiluminescence systems, for example in chemiluminescent illumination rods, in luminescent immunoassays or other luminescent detection methods.

Use of the transition metal complexes as dyes or luminescent dyes as signal colors, preferably for the optical emphasis of inscriptions and drawings or other graphical products, for individualizing signs and other articles in which a particular optical color impression is to be achieved.

Use of the transition metal complexes as dyes or luminescent dyes in dye lasers, preferably as luminescent dyes for generating laser beams.

Use of the transition metal complexes as active substances for nonlinear optics, for example for frequency doubling and frequency tripling of laser light.

Use of the transition metal complexes as rheology improvers.

Use of the transition metal complexes as dyes in photovoltaic applications for the conversion of electromagnetic radiation to electrical energy.

The examples which follow provide additional illustration of the invention.

EXAMPLES

Example 1: Preparation of the Transition Metal-Carbene Complex

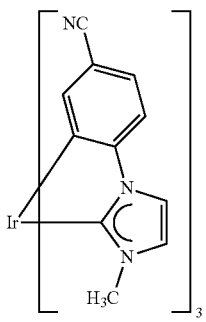

Preparation of the Carbene Precursor Compound a)

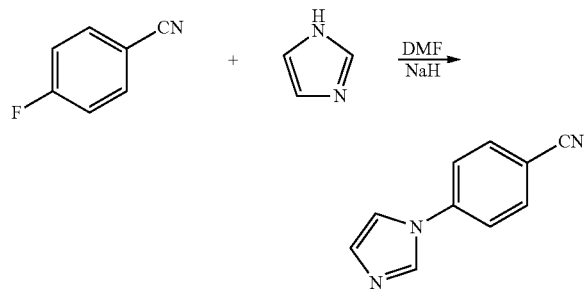

Under nitrogen blanketing, 1500 ml of dry dimethylformamide (DMF) are initially charged in a 1000 ml four-necked flask and 72.67 g (0.6 mol) of 4-fluorocyanobenzene and 61.2 g (0.9 mol) of imidazole, and finally 21.6 g (0.9 mol) of sodium hydride, are added. The reaction mixture is heated to 100° C., stirred at this temperature for 4 hours and finally stirred at room temperature overnight. The reaction mixture is then poured onto water and the resulting mixture is extracted repeatedly with dichloromethane. The organic phase is dried, concentrated on a rotary evaporator and finally dried at 60° C. under reduced pressure. The yield is 94 g (corresponding to 93% of theory).

$^1$H NMR (400 MHz, CDCl$_3$): δ=7.27 (s, 1H); 7.35 (s, 1H); 7.54 (d, J=8.8 Hz, 2H); 7.81 (d, J=8.8 Hz, 2H); 7.95 (s, 1H).

b)

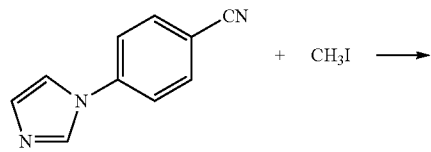

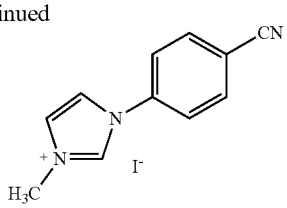

56 g (0.33 mol) of the 4-N-imidazolylbenzonitrile obtained from a) are dissolved in 560 ml of anhydrous tetrahydrofuran in a 2000 ml one-neck flask with condenser, admixed with 234.2 g (1.65 mol) of methyl iodide, stirred briefly and left to stand without further stirring for 48 hours. The solid flask contents are subsequently slurried with ethanol, filtered off with suction and washed with ethanol until the effluent is virtually colorless. The residue is dried under reduced pressure at 70° C. The yield is 81.54 g (corresponding to 79.7% of theory).

$^1$H NMR (400 MHz, DMSO): δ=3.97 (s, 3H); 8.00-8.04 (m, 3H); 8.22 (d, J=9.0 Hz, 2H); 8.40 (dd, J=1.8, 1.8 Hz, 1H); 9.91 (s, 1H).

Elemental analysis (calculated value for empirical formula $C_{11}H_{10}IN_3$):

|  | Calculated (% by wt.) | found (% by wt.) |
|---|---|---|
| Iodine | 40 | 40.9 |
| Carbon | 42.4 | 42.6 |
| Nitrogen | 13.5 | 13.6 |
| Hydrogen | 3.3 | 2.93 | c)

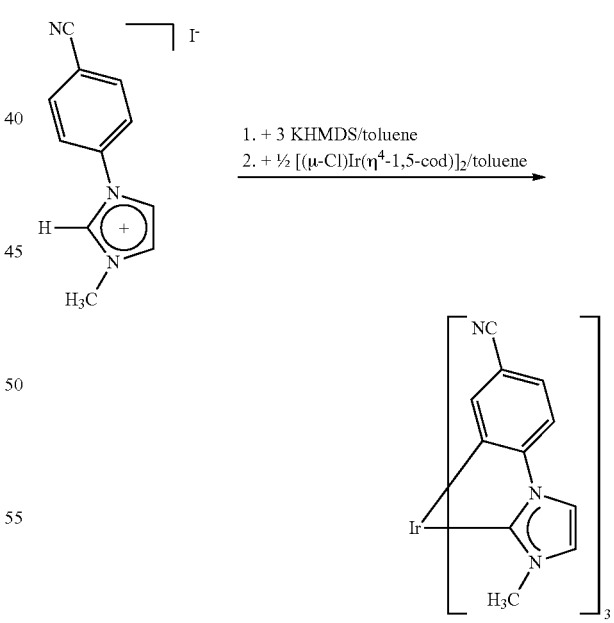

A 500 l three-neck flask is initially charged with 10 g (32 mmol) of imidazolium iodide in 150 ml of toluene and 64.3 ml of potassium bis(trimethylsilyl)amide (0.5 M in toluene, 32 mmol) are added at room temperature within 30 minutes. The mixture is left to stir at room temperature for 30 minutes. 2.16 g (3.2 mmol) of [(μ-Cl)(η$^4$-1,5-cod)Ir]$_2$ are then dissolved in 200 ml of toluene and admixed dropwise with the salt mixture at room temperature. The reaction mixture is stirred at room temperature for one hour, at 70° C. for 2 hours and then under reflux overnight. The mixture is subsequently concentrated to dryness and the residue is extracted with methylene chloride. After again concentrating to dryness, the brown residue is subjected to purification by column chromatography. 1.15 g of a yellow powder (24% of theory) are obtained.

$^1$H NMR (CD$_2$Cl$_2$, 500 MHz): δ=7.42 (m, 2H), 7.35 (m, 1H), 7.20-7.00 (m, 6H), 6.95, 6.90, (each s, 1H), 6.77, 6.76, 6.74 6.69 (each m, 1H) (each CH$_{Ph}$ or NCHCHN), 2.94 (m, 6H, CH$_3$), 2.87 (s, 3H, CH$_3$).

$^{13}$C NMR (CD$_2$Cl$_2$, 125 MHz): δ=173.3, 171.8, 170.8 (NCN), 150.8, 150.1, 149.7, 149.4, 148.8, 147.0 (Cq), 141.4, 141.2, 139.5, 125.1, 125.0, 124.8, 121.6, 121.3, 121.1, 114.3, 114.2, 114.1, 110.0, 109.9, 109.5 (CH$_{Ph}$, NCHCHN), 119.9, 119.8, 119.7, 107.5, 107.1, 106.9 (Cq, CN), 36.5 (intensity×2), 35.3 (CH$_3$).

Visual spectroscopy: λ=459 nm, 436 nm (emission maximum, shoulder in polymethyl methacrylate (PMMA))

Quantum yield: 57% (in PMMA)

Elemental analysis (calculated value for empirical formula IrC$_{33}$H$_{24}$N$_9$):

|  | calculated (% by wt.) | found (% by wt.) |
| --- | --- | --- |
| Carbon | 53.7 | 54.0 |
| Nitrogen | 17.1 | 16.2 |
| Hydrogen | 3.3 | 3.7 |

Thermogravimetry/differential thermoanalysis (heating rate: 5K/min):

Loss of solvent at from approx. 100° C. to 160° C.

Start of decomposition from approx. 370° C.

HPLC: >99 area % (column: Purospher Si 80, eluent: heptane/isopropanol=70/30 (% by vol.))

Example 2: Production of an OLED a)

The ITO substrate used as an anode is cleaned first with commercial detergents for LCD production (Deconex® 20NS and 25ORGAN-ACID® neutralizing agent) and then in an ultrasound bath in an acetone/isopropanol mixture. To remove possible organic residues, the substrate is exposed to a continuous ozone flow in an ozone oven for a further 25 minutes. This treatment also improves the hole injection of the ITO.

Afterward, the organic materials specified below are applied to the cleaned substrate by vapor deposition at a rate of approx. 2 nm/min at about 10$^{-7}$ mbar. As the hole conductor, 1-TNATA (4,4',4''-tris(N-(naphth-1-yl)-N-phenylamino)triphenylamine) is applied first to the substrate in a layer thickness of 17.5 nm. This is followed by the application by vapor deposition of a 9.5 nm-thick exciton blocker layer of the compound C1

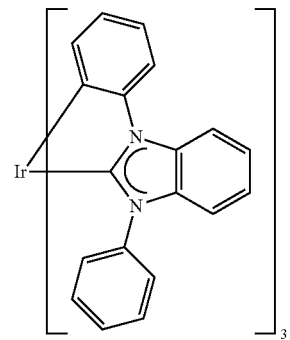

(C1)

(for the preparation, see Ir complex (7) in the application PCT/EP/04/09269).

Subsequently, a mixture of 34% by weight of the compound 1 c)

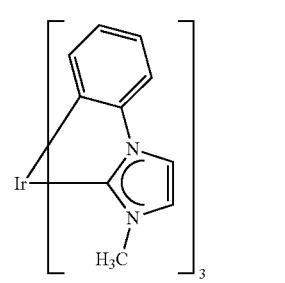

(1c))

from example 1 c) and 66% by weight of the compound C2

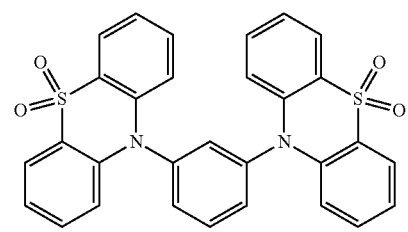

(C2)

(1,3-phenylene-10,10'-bis(phenothiazine) 5,5'-dioxide) is applied by vapor deposition in a thickness of 20 nm, the former compound serving as the emitter, the latter as the matrix material. Afterward, a hole blocker and electron conductor layer of 2,9-dimethyl-4,7-diphenyl-1,10-phenanthroline (BCP) in a thickness of 47.5 nm, a 0.75 nm-thick lithium fluoride layer and finally a 110 nm-thick Al electrode are applied by vapor deposition.

To characterize the OLED, the electroluminescence spectra are recorded at various currents and voltages. In addition, the current-voltage characteristic is measured in combination with the emitted light output. The light output can be converted to photometric parameters by calibration with a photometer.

For the OLED described, the following electrooptical data are obtained:

| | |
|---|---|
| Emission maximum | 466 nm |
| CIE(x, y) | 0.17; 0.21 |
| Photometric efficiency | 11.7 cd/A |
| Power efficiency | 9.9 lm/W |
| External quantum yield | 7.3% |
| Photometric efficiency at an luminance of 100 cd/m$^2$ | 10.3 cd/A |
| Maximum luminance | 2700 cd/m$^2$ |

The compound C2 was prepared as follows:

i) Preparation of 1,3-phenylene-10,10'-bis(phenothiazine) according to K. Okada et al., J. Am. Chem. Soc. 1996, 118, 3047-3048.

18.5 g (91.9 mmol) of phenothiazine, 15.6 g (46.3 mmol) of 98% 1,3-diiodobenzene, 19.4 g (140 mmol) of potassium carbonate and 1.16 g (18.3 mmol) of activated copper powder were heated to 200° C. and stirred at this temperature for 24 h. The reaction mixture was cooled to 140° C. and then admixed with 200 ml of ethyl acetate. The suspension was heated to boiling under reflux for one hour and subsequently hot-filtered. The filtrate was diluted with 300 ml of methanol, and the solid precipitated out and was filtered off with suction, washed with methanol and dried at 80° C. under reduced pressure. 8.91 g of pink solid having an m.p. of 186-188° C. were obtained.

ii) Preparation of 1,3-phenylene-10,10'-bis(phenothiazine) 5,5'-dioxide (C2)

6.28 g (13.3 mmol) of 1,3-phenylene-10,10'-bis(phenothiazine) were dissolved in 220 ml of methylene chloride. After stirring at room temperature for 15 minutes, 17.9 g (79.9 mmol) of 77% m-chloroperbenzoic acid were added in portions. The reaction solution was stirred at room temperature for 24 h, in the course of which a solid precipitated out. The solution was filtered, and the residue was washed with methylene chloride and suction-dried. The solid was suspended in hot water. The aqueous suspension was adjusted to pH 11 with 5% potassium hydroxide solution and subsequently hot-filtered. The residue was washed with hot water and dried at 80° C. under reduced pressure. The solid (5.07 g) was recrystallized from dimethylformamide. 3.72 g of colorless microcrystals having an m.p. of 412 g were obtained in analytically pure form, whose solution in toluene fluoresced at λ=375 nm (S).

b)

The ITO substrate is pretreated as described under a).

Afterward, the organic materials specified below are applied to the cleaned substrate by vapor deposition at a rate of approx. 2 nm/min at about 10$^{-7}$ mbar. As the hole conductor, 1-TNATA (4,4',4"-tris(N-(naphth-1-yl)-N-phenylamino)triphenylamine) is applied first to the substrate in a layer thickness of 15 mm. This is followed by the application by vapor deposition of a 9 mm-thick exciton blocker layer of the compound C1.

Subsequently, a mixture of 55% by weight of the compound 1 c) and 45% by weight of 1,3-bis(N-carbazolyl)benzene is applied by vapor deposition in a thickness of 16 nm, the former compound serving as the emitter, the latter as the matrix material. Afterward, a hole blocker and electron conductor layer of BCP in a thickness of 45 nm, a 0.75 nm-thick lithium fluoride layer and finally a 110 nm-thick Al electrode are applied by vapor deposition.

To characterize the OLED, the electroluminescence spectra are recorded at various currents and voltages. In addition, the current-voltage characteristic is measured in combination with the emitted light output. The light output can be converted to photometric parameters by calibration with a photometer.

For the OLED described, the following electrooptical data are obtained:

| | |
|---|---|
| Emission maximum | 476 nm |
| CIE(x, y) | 0.21; 0.30 |
| Photometric efficiency | 10.0 cd/A |
| Power efficiency | 11.6 lm/W |
| External quantum yield | 5.0% |
| Photometric efficiency at an luminance of 100 cd/m$^2$ | 4.0 cd/A |
| Maximum luminance | 3500 cd/m$^2$ | c)

The ITO substrate is pretreated as described under a).

Subsequently, PEDT:PSS (poly(3,4-ethylenedioxythiophene) poly(styrenesulfonate)) (Baytron® P VP AI 4083) is spin-coated from aqueous solution onto the substrate in a thickness of 46 nm and the emitter layer is applied in a thickness of approx. 48 nm from PMMA dissolved in chlorobenzene (16.5 mg of PMMA for 1 ml of chlorobenzene) and the emitter substance 1 c). The concentration of the emitter corresponds to a 30% by weight doping of PMMA. Afterward, a hole blocker and electron conductor layer of BCP in a thickness of 52.5 nm, a 0.75 nm-thick lithium fluoride layer and finally a 110 nm-thick Al electrode are applied by vapor deposition.

To characterize the OLED, electroluminescence spectra are recorded at various currents and voltages. In addition, the current-voltage characteristic is measured in combination with the emitted light output. The light output may be converted to photometric parameters by calibration with a photometer.

For the OLED described, the following electrooptical data are obtained:

| | |
|---|---|
| Emission maximum | 460 nm |
| Photometric efficiency | 4.3 cd/A |
| Power efficiency | 1.1 lm/W |
| External quantum yield | 3.5% |
| Photometric efficiency at an luminance of 100 cd/m$^2$ | 1.2 cd/A |
| Maximum luminance | 150 cd/m$^2$ |

Photoluminescence ("PL") of the iridium-carbene complexes

| Complex | PL in toluene | | | | PL in polymethacrylate ("PMMA") film | | | | PL in powder | |
|---|---|---|---|---|---|---|---|---|---|---|
| | $\lambda_{em}$* [nm] | QY** [%] | CIE x | CIE y | $\lambda_{em}$* [nm] | QY** [%] | CIE x | CIE y | CIE x | CIE y |
| Ir(pipic)$_3$ | 398 | 1 | 0.161 | 0.080 | — | — | — | — | 0.160 | 0.059 |
| Ir(cn-pibic)$_3$ | 382-454 | 7 | 0.151 | 0.095 | 454 | 70 | 0.150 | 0.096 | — | — |

-continued

| | Photoluminescence ("PL") of the iridium-carbene complexes | | | | | | | | | |
|---|---|---|---|---|---|---|---|---|---|---|
| | PL in toluene | | | | PL in polymethacrylate ("PMMA") film | | | | PL in powder | |
| Complex | $\lambda_{em}$* [nm] | QY** [%] | CIE x | CIE y | $\lambda_{em}$* [nm] | QY** [%] | CIE x | CIE y | CIE x | CIE y |
| Ir(psmbic)$_3$ | 472 | <1 | 0.251 | 0.270 | 472 | 4 | 0.160 | 0.199 | 0.266 | 0.248 |
| Ir(cl-pmic)$_3$ | 407 | 4 | 0.164 | 0.062 | 393, 460 | 2 | 0.180 | 0.149 | 0.195 | 0.212 |
| Ir($^t$bu-cn-pmic)$_3$ | 431-455 | 26 | 0.149 | 0.099 | 458 | 55 | 0.149 | 0.105 | — | — |
| fac-Ir(cn-pmic)$_3$ | 470 | 8 | 0.174 | 0.234 | 452 | 73 | 0.150 | 0.092 | 0.277 | 0.437 |
| Ir(me$_2$-cn-pmic)$_3$ | — | — | — | — | 464 | 67 | 0.149 | 0.141 | 0.279 | 0.382 |
| Ir(cn-pmbic)$_3$ | — | — | — | — | 454 | 78 | 0.150 | 0.095 | 0.220 | 0.262 |
| Ir(pymic)$_3$ | 403 | 7 | 0.165 | 0.073 | 478 | — | 0.182 | 0.271 | 0.564 | 0.410 |
| Ir(btmbic)$_3$ | — | — | — | — | 493, 527, 557 | — | 0.318 | 0.547 | — | — |
| Ir(pombic)$_3$ | 408, 433, 458 | — | 0.195 | 0.138 | 407, 433, 457 | 10 | 0.156 | 0.082 | 0.440 | 0.441 |

*Wavelength(s) $\lambda_{em}$ of the emission maximum or of the emission maxima
**Quantum yield.

The PL measurements in toluene were performed with an emitter concentration of 2 mg/l in quartz cuvettes (10×10 mm). The excitation wavelength was 325 nm (HeCd laser) and the emission was detected at an angle of 90 degrees by means of fiber optics in a diode array spectrometer.

The PL measurements in PMMA were performed with an emitter doping of 2%. These were produced as follows: 2 mg/l of emitter were dissolved in a 10% PMMA solution in dichloromethane (Mw 120 kD) and knife-coated onto a microscope slide with a 60 µm doctor blade. The excitation wavelength was 325 nm (HeCd laser); the excitation was at right angles to the microscope slide and the emission was detected at an angle of 45 degrees by means of fiber optics in a diode array spectrometer.

For the OLED described, the following electrooptical data are obtained:

| Emission maximum | 476 nm |
|---|---|
| CIE(x, y) | 0.21; 0.30 |
| Photometric efficiency | 10.0 cd/A |
| Power efficiency | 11.6 lm/W |
| External quantum yield | 5.0% |
| Photometric efficiency at an luminance of 100 cd/m$^2$ | 4.0 cd/A |
| Maximum luminance | 3500 cd/m$^2$ | c)
The ITO substrate is pretreated as described under a).
Subsequently, PEDT:PSS (poly(3,4-ethylenedioxythiophene) poly(styrenesulfonate)) (Baytron® P VP AI 4083) is spin-coated from aqueous solution onto the substrate in a thickness of 46 nm and the emitter layer is applied in a thickness of approx. 48 nm from PMMA dissolved in chlorobenzene (16.5 mg of PMMA for 1 ml of chlorobenzene) and the emitter substance 1 c). The concentration of the emitter corresponds to a 30% by weight doping of PMMA. Afterward, a hole blocker and electron conductor layer of BCP in a thickness of 52.5 nm, a 0.75 nm-thick lithium fluoride layer and finally a 110 nm-thick Al electrode are applied by vapor deposition.

To characterize the OLED, electroluminescence spectra are recorded at various currents and voltages. In addition, the current-voltage characteristic is measured in combination with the emitted light output. The light output may be converted to photometric parameters by calibration with a photometer.

For the OLED described, the following electrooptical data are obtained:

| Emission maximum | 460 nm |
|---|---|
| Photometric efficiency | 4.3 cd/A |
| Power efficiency | 1.1 lm/W |
| External quantum yield | 3.5% |
| Photometric efficiency at an luminance of 100 cd/m$^2$ | 1.2 cd/A |
| Maximum luminance | 150 cd/m$^2$ |

What is claimed is:
1. An uncharged transition metal-carbene complex of the formula I

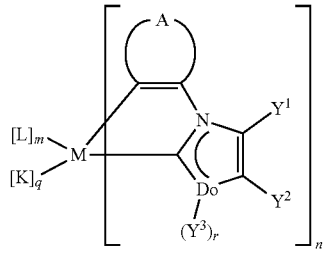

(I)

where the variables are each defined as follows:
M is a metal atom selected from the group consisting of Co, Rh, Ir, Nb, Pd, Pt, Fe, Ru, Os, Cr, Mo, W, Mn, Re, Cu, Ag and Au in any oxidation state possible for the particular metal atom;
L is a mono- or dianionic ligand which may be mono- or bidentate;
K is an uncharged mono- or bidentate ligand selected from the group consisting of phosphines; phosphonates and derivatives thereof; arsenates and derivatives thereof; phosphites; CO; pyridines; nitriles, monoolefins and conjugated dienes which form a π-complex with M;
n is the number of carbene ligands, where n is at least 1 and the carbene ligands in the complex of formula I, when n>1, may be the same or different;
m is the number of ligands L, where m may be 0 or ≥1 and the ligands L, when m>1, may be the same or different;

q is the number of ligands K, where q may be 0 or ≥1 and the ligands K, when q>1, may be the same or different, where the sum of n+m+q depends upon the oxidation state and coordination number of the metal atom M and upon the denticity and the charge of the ligands, with the condition that n is at least 1;

Do is a donor atom selected from the group consisting of N, O and S;

r is 1 when Do is N, and r is 0 when Do is O or S;

$Y^1$, $Y^2$ are each independently hydrogen, alkyl, aryl, heteroaryl or alkenyl;

or $Y^1$ and $Y^2$, together with the carbon atoms to which they are bonded, form a six-membered aromatic ring which may comprise one or two nitrogen atoms, and is optionally fused to a further ring which is optionally fused and optionally comprises heteroatoms;

$Y^3$ is hydrogen or alkyl;

or $Y^3$ and $Y^2$, together with the donor atom Do and the carbon atom to which $Y^2$ is bonded, form a five- or six-membered ring which, apart from the donor atom Do, may also comprise a further heteroatom selected from the group consisting of N, O and S;

A is a bridge having four atoms, so that the group

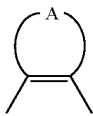

forms a benzene ring, wherein said benzene ring is substituted at the 4-position with a CN group and said benzene ring is optionally further substituted by substituents selected from the group consisting of alkyl, alkyloxy, alkylthio, aryl, aryloxy, arylthio, halogen, CHO, alkylcarbonyl, arylcarbonyl, carboxyl, alkyloxycarbonyl, aryloxycarbonyl, hydroxysulfonyl, alkyloxysulfonyl, aryloxysulfonyl, $NO_2$ and NO, where $Y^1$, together with a group selected from chemical single bond, $C(Y^4)_2$, C(O), O, S, S(O), $SO_2$ and $NY^5$, may optionally form a two-membered bridge B to that carbon atom of the bridge A which is in the α-position to the carbon atom which is bonded to the nitrogen atom of the carbene unit of the carbene ligand; and $Y^4$, $Y^5$ are each independently hydrogen, alkyl, aryl or heteroaryl, and the two $Y^4$ groups in the $C(Y^4)_2$ bridge may be varied independently of one another.

2. The complex of formula I as claimed in claim 1, wherein

M is selected from the group consisting of Rh, Ir, Pd, Pt, Ru and Os in any oxidation state possible for the particular metal atom.

3. The complex of formula I as claimed in claim 1, wherein n is at least 2 and the carbene ligands may be the same or different;

m is 0 or ≥1 and the ligands L, when m>1, may be the same or different; and q is 0 or ≥1 and the ligands K, when q>1, may be the same or different.

4. The complex of formula I as claimed in claim 1, wherein n is at least 2 and the carbene ligands may be the same or different; and m, q are each 0.

5. The complex of formula I as claimed in claim 1, wherein n is at least 2 and the carbene ligands are the same; and m and q are each 0.

6. An organic light-emitting diode comprising an uncharged transition metal-carbene complex of general formula I as claimed in claim 1.

7. A device selected from the group consisting of stationary visual display units of computers, televisions, visual display units in printers, kitchen appliances and advertising panels, illuminations, and information panels; and mobile visual display units in mobile telephones, laptops, vehicles and destination displays in buses and trains, comprising an organic light-emitting diode as claimed in claim 6.

8. A process for preparing a transition metal-carbene complex of a formula I as claimed in claim 1 by deprotonating a ligand precursor corresponding to the particular carbene ligand and subsequently or simultaneously reacting it with a suitable metal complex comprising the desired metal.

9. A light-emitting layer comprising at least one transition metal-carbene complex of formula I as claimed in claim 1.

10. An organic light-emitting diode comprising a light-emitting layer as claimed in claim 9.

11. A device selected from the group consisting of stationary visual display units of computers, televisions, visual display units in printers, kitchen appliances and advertising panels, illuminations, and information panels; and mobile visual display units in mobile telephones, laptops, vehicles and destination displays in buses and trains, comprising an organic light-emitting diode as claimed in claim 10.

12. A method of bulk coloring a polymeric material comprising adding an uncharged transition metal-carbene complex of formula I as claimed in claim 1 to said polymeric material.

13. The complex of formula I as claimed in claim 1, wherein $Y^3$ is a hydrogen or alkyl group.

14. The complex of formula I as claimed in claim 1, wherein the complex is of the formula:

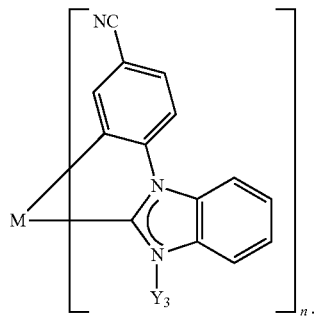

* * * * *